(12) United States Patent
Eguchi

(10) Patent No.: US 11,696,734 B2
(45) Date of Patent: Jul. 11, 2023

(54) RADIOGRAPHY APPARATUS

(71) Applicant: FUJIFILM Corporation, Tokyo (JP)

(72) Inventor: Koichi Eguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/032,937

(22) Filed: Sep. 25, 2020

(65) Prior Publication Data

US 2021/0093268 A1 Apr. 1, 2021

(30) Foreign Application Priority Data

Sep. 30, 2019 (JP) .................. 2019-180016

(51) Int. Cl.
*A61B 6/00* (2006.01)
(52) U.S. Cl.
CPC .......... *A61B 6/4441* (2013.01); *A61B 6/4411* (2013.01); *A61B 6/4476* (2013.01); *A61B 6/586* (2013.01)
(58) Field of Classification Search
CPC ..... A61B 6/105; A61B 6/4405; A61B 6/4441; A61B 6/4476; A61B 6/586; A61B 6/4411; A61B 6/4452
See application file for complete search history.

(56) References Cited

U.S. PATENT DOCUMENTS

| | | | | |
|---|---|---|---|---|
| 5,073,917 A | * | 12/1991 | Van Endschot | A61B 6/4441 378/197 |
| 6,113,265 A | * | 9/2000 | Babler | A61B 6/4441 378/197 |
| 6,142,667 A | * | 11/2000 | Pattee | A61B 6/447 378/197 |
| 6,374,937 B1 | * | 4/2002 | Galando | A61B 6/467 378/198 |
| 6,609,826 B1 | * | 8/2003 | Fujii | A61B 6/56 378/197 |
| 6,880,691 B2 | * | 4/2005 | Simmons | A61B 6/4441 378/198 |
| 9,220,471 B2 | * | 12/2015 | Noda | A61B 6/4233 |
| 11,109,820 B2 | * | 9/2021 | Hong | A61B 6/4441 |

(Continued)

FOREIGN PATENT DOCUMENTS

| | | |
|---|---|---|
| DE | 10 2004 022 804 B3 | 9/2005 |
| DE | 102004022804 * | 9/2005 |

(Continued)

OTHER PUBLICATIONS

Machine Translation of JP2002102214 (Year: 2002).*

(Continued)

*Primary Examiner* — Dani Fox
*Assistant Examiner* — Soorena Kefayati
(74) *Attorney, Agent, or Firm* — Birch, Stewart, Kolasch & Birch, LLP

(57) ABSTRACT

A radiography apparatus includes: an irradiation unit that emits radiation; an arm that can hold the irradiation unit and an image receiving unit in a facing posture; a first rotation mechanism that rotates the arm; and a friction mechanism that is switchable between a first state in which a frictional force is applied to the arm in a direction opposite to a direction in which the arm is rotated and a second state in which the frictional force applied to the arm is less than that in the first state.

15 Claims, 24 Drawing Sheets

(56) References Cited

U.S. PATENT DOCUMENTS

| | | | | |
|---|---|---|---|---|
| 2003/0053599 A1* | 3/2003 | Meyer | .................. | A61B 6/04 378/196 |
| 2004/0052335 A1* | 3/2004 | Pillai | .................. | A61B 6/105 378/198 |
| 2005/0003914 A1* | 1/2005 | Simmons | .................. | A61B 6/4405 474/138 |
| 2005/0006196 A1* | 1/2005 | Simmons | .................. | A61B 6/4441 192/95 |
| 2005/0129181 A1* | 6/2005 | Shinoda | .................. | A61B 6/547 378/209 |
| 2008/0069309 A1* | 3/2008 | Dorre | .................. | A61B 6/467 378/197 |
| 2009/0082661 A1* | 3/2009 | Saladin | .................. | A61B 6/4464 600/415 |
| 2009/0216067 A1* | 8/2009 | Lebosse | .................. | A61B 34/30 600/13 |
| 2012/0106701 A1* | 5/2012 | Meek | .................. | H05G 1/02 474/84 |
| 2012/0212308 A1* | 8/2012 | Herrmann | .................. | A61B 6/4441 335/219 |
| 2012/0300909 A1* | 11/2012 | Simmons | .................. | A61B 6/4441 378/197 |
| 2012/0314843 A1* | 12/2012 | Limmer | .................. | A61B 6/44 378/197 |
| 2012/0325611 A1* | 12/2012 | Klemm | .................. | A61B 6/10 192/56.1 |
| 2013/0253485 A1* | 9/2013 | Fehre | .................. | H02P 29/04 606/2.5 |
| 2013/0272499 A1* | 10/2013 | Simmons | .................. | G01N 23/04 378/197 |
| 2013/0279663 A1* | 10/2013 | Barker | .................. | A61B 6/54 378/197 |
| 2015/0223767 A1* | 8/2015 | Sehnert | .................. | A61B 6/547 378/42 |
| 2015/0313564 A1* | 11/2015 | Narabu | .................. | A61B 6/022 378/42 |
| 2016/0296185 A1* | 10/2016 | Gemmel | .................. | A61B 6/547 |
| 2017/0238890 A1* | 8/2017 | Limmer | .................. | A61B 6/4441 |
| 2018/0021003 A1* | 1/2018 | Kim | .................. | A61B 6/584 378/189 |
| 2018/0271461 A1* | 9/2018 | Simmons | .................. | A61B 6/44 |
| 2018/0298970 A1* | 10/2018 | Daugirdas | .................. | A61B 6/4476 |

FOREIGN PATENT DOCUMENTS

| | | | | |
|---|---|---|---|---|
| DE | 102004022804 B3 * | 9/2005 | ........... | A61B 6/4405 |
| EP | 0 231 969 A1 | 8/1987 | | |
| EP | 0 430 338 A1 | 6/1991 | | |
| EP | 1 397 995 A1 | 3/2004 | | |
| EP | 3 391 825 A1 | 10/2018 | | |
| JP | 62-183746 A | 8/1987 | | |
| JP | 6-70918 A | 3/1994 | | |
| JP | 10-33516 A | 2/1998 | | |
| JP | 10-225450 A | 8/1998 | | |
| JP | 2002102214 A * | 4/2002 | | |
| JP | 2004-73356 A | 3/2004 | | |
| JP | 2008-245726 A | 10/2008 | | |
| JP | 2012-525899 A | 10/2012 | | |
| JP | 2018-175872 A | 11/2018 | | |
| WO | WO-2020239187 A1 * | 12/2020 | ........... | A61B 6/4405 |

OTHER PUBLICATIONS

Machine translation of JP2002102214 (Year: 2020).*
Machine translation of DE102004022804 (Year: 2004).*
Machine translation of WO2020239187 (Year: 2020).*
Extended European Search Report for European Application No. 20198792.2, dated Feb. 8, 2021.
Japanese Office Action for corresponding Japanese Application No. 2019-180016, dated Feb. 15, 2022, with English translation.
Japanese Notice of Reasons for Refusal for corresponding Japanese Application No. 2019-180016, dated May 17, 2022, with an English translation.

* cited by examiner

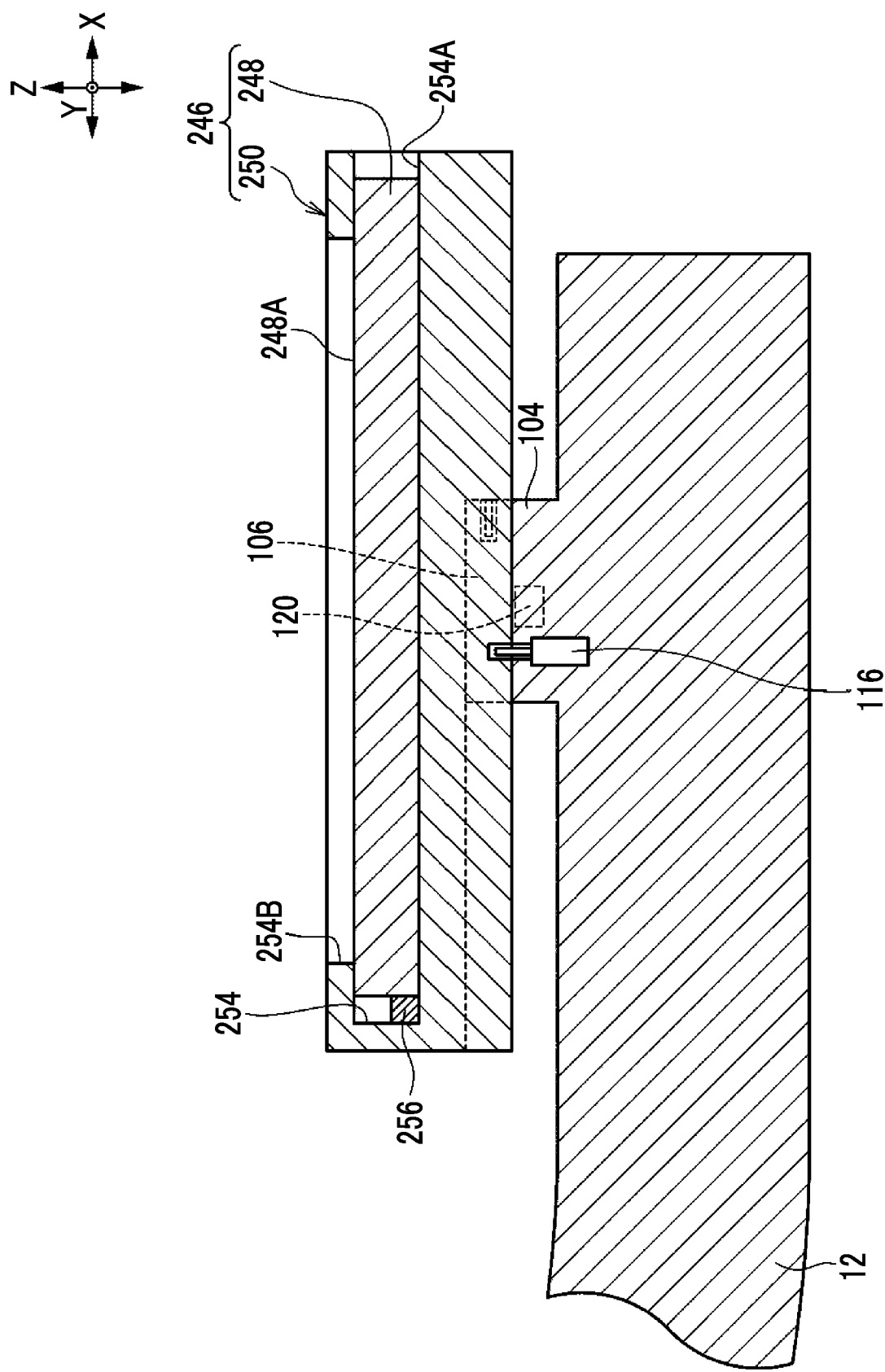

RADIOGRAPHY APPARATUS

CROSS-REFERENCE TO RELATED APPLICATIONS

The present application claims priority under 35 U.S.C. § 119 to Japanese Patent Application No., 2019-180016 filed on Sep. 30, 2019. The above application is hereby expressly incorporated by reference, in its entirety, into the present application.

BACKGROUND

1. Technical Field

The present disclosure relates to a radiography apparatus.

2. Description of the Related Art

A radiography apparatus (X-ray apparatus) has been known which includes an arm having two ends. An irradiation unit (X-ray tube) that emits radiation is provided at one end of the arm. An image receiving unit (image receiving device) that receives the radiation emitted from the irradiation unit is provided at the other end of the arm. This arm is supported so as to be rotatable with respect to a main body of the radiography apparatus. The arm is rotated such that the irradiation unit and the image receiving unit can be positioned in any posture around a subject while maintaining a relative position. In addition, in a radiography apparatus disclosed in JP1994-070918A (JP-H06-070918A), an arm can be manually rotated.

SUMMARY

In a case in which the arm is manually operated, the load of an operation force may be small or large according to circumstances. For example, a case in which the radiography apparatus is used during surgery is considered. In this case, it is preferable that the load of the operation force of the arm is small in a positioning stage before surgery. After the surgery is started, it is preferable that the arm is not inadvertently rotated due to contact with a person.

In particular, in the case of an arm that holds both the irradiation unit and the image receiving unit, the weight of the arm is greater than that of an arm that holds only the irradiation unit. Therefore, there is a great need to reduce the load of the operation force due to a manual operation. In a case in which the load of the operation force is always small, inadvertent rotation is likely to occur, which is not preferable. JP1994-070918A (JP-H06-070918A) does not disclose and suggest the problems and measures. Therefore, there has been a demand for measures to solve these problems.

An object of the technology according to the present disclosure is to provide a radiography apparatus that can change a load due to a manual operation force of an arm.

According to a first aspect of the present disclosure, there is provided a radiography apparatus comprising: an irradiation unit that emits radiation; an arm that is capable of holding the irradiation unit and an image receiving unit that receives the radiation, which has been emitted from the irradiation unit and transmitted through a subject, in a facing posture; a support portion that supports the arm; a displacement mechanism that displaces the arm with respect to the support portion; and a friction mechanism that is switchable between a first state in which a frictional force is applied to the arm in a direction opposite to a direction in which the arm is displaced and a second state in which the frictional force applied to the arm is less than the frictional force in the first state.

According to the above-mentioned configuration, the radiography apparatus comprises the displacement mechanism that displaces the arm and the friction mechanism that is switchable between the first state in which the frictional force is applied to the arm in the direction opposite to the direction in which the arm is displaced and the second state in which the frictional force applied to the arm is less than that in the first state. Therefore, the friction mechanism is switched between the first state and the second state to change a load due to the manual operation force of the arm.

According to a second aspect of the present disclosure, the radiography apparatus according to the first aspect may further comprise an operation portion that switches the friction mechanism between the first state and the second state.

According to the above-mentioned configuration, the operator can optionally switch the frictional force. For example, before surgery, it is possible to reduce the frictional force such that positioning is performed with a small force. During surgery, it is possible to increase the frictional force in order to prevent the arm from being inadvertently rotated due to the application of an unintended external force to the arm such as the collision of the operator with the arm.

According to a third aspect of the present disclosure, in the radiography apparatus according to the first aspect or the second aspect, the arm may be displaced by only a manual operation.

According to the above-mentioned configuration, the arm is not displaced by an electromotive force, but can be displaced by only a manual operation. Therefore, it is possible to reduce the size and weight of the entire radiography apparatus. In many cases, a large-sized radiography apparatus includes a mechanism that electrically displaces the arm. In general, in the large-sized apparatus, the operation force of the arm is controlled through a complicated mechanism such as an electric mechanism.

Here, the friction mechanism according to the technology of the present disclosure can switch the operation force of the arm with a relatively simple structure even in a case in which the arm is displaced by only a manual operation to reduce the size and weight of the apparatus. Therefore, the technology of the present disclosure is particularly effective for an apparatus with a small size and weight in which the arm is displaced by only a manual operation.

According to a fourth aspect of the present disclosure, in the radiography apparatus according to any one of the first to third aspects, the displacement mechanism may be a rotation mechanism that rotates the arm.

According to the above-mentioned configuration, a load is applied in the rotation operation of rotating the arm, as compared to an operation of sliding the arm in the horizontal direction. Therefore, this configuration is particularly effective in a case in which the friction mechanism capable of switching the frictional force is combined with the rotation mechanism.

According to a fifth aspect of the present disclosure, in the radiography apparatus according to the fourth aspect, the image receiving unit may be attachable to and detachable from the arm.

According to the above-mentioned configuration, in a case in which the arm is rotated and the image receiving unit is attachable and detachable, a weight balance changes greatly during the detachment of the image receiving unit. As a result, inadvertent rotation is likely to occur. Therefore, for example, in a case in which the image receiving unit is detached, the frictional force is increased to suppress inadvertent rotation.

According to a sixth aspect of the present disclosure, the radiography apparatus according to the fifth aspect may further comprise: an attachment and detachment detection unit that detects whether or not the image receiving unit is detached from the arm; and a control unit that performs control to switch the friction mechanism to the first state in a case in which the attachment and detachment detection unit detects that the image receiving unit is detached from the arm and to switch the friction mechanism to the second state in a case in which the attachment and detachment detection unit detects that the image receiving unit is attached to the arm.

In a case in which the image receiving unit is detached from the arm, the weight balance of the arm may change and the arm may be inadvertently rotated. Here, according to the above-mentioned configuration, the frictional force is increased in operative association with the detachment of the image receiving unit. Therefore, it is possible to suppress the inadvertent rotation of the arm even in a case in which the image receiving unit is detached.

According to a seventh aspect of the present disclosure, in the radiography apparatus according to the sixth aspect, the frictional force in the first state may be greater than a maximum weight of the image receiving unit that is capable of being attached to the arm.

According to the above-mentioned configuration, since the frictional force in the first state is greater than the weight of the image receiving unit, a change in the weight balance of the arm in a case in which the image receiving unit is detached can be absorbed by the frictional force and it is possible to further suppress the inadvertent rotation of the arm.

According to an eighth aspect of the present disclosure, the radiography apparatus according to any one of the fourth to seventh aspects may further comprise an electromagnetic brake that locks the rotation of the arm by the rotation mechanism.

According to the above-mentioned configuration, the radiography apparatus includes the electromagnetic brake that locks the rotation of the arm in addition to the friction mechanism. Therefore, the electromagnetic brake locks the rotation of the arm to prohibit the rotation of the arm as necessary.

According to a ninth aspect of the present disclosure, in the radiography apparatus according to any one of the fourth to eighth aspects, the rotation mechanism may have a rotation shaft that is rotated with the rotation of the arm and the friction mechanism may comprise a friction shaft, a frictional force generation unit that is attached to the friction shaft and generates a frictional force, and a clutch that switches connection and disconnection between the rotation shaft and the friction shaft to switch between the first state and the second state.

According to the above-mentioned configuration, the components of the rotation mechanism and the components of the friction mechanism are operatively associated with each other to reduce the size of each mechanism, as compared to a case in which the rotation mechanism and the friction mechanism are independently configured.

According to a tenth aspect of the present disclosure, in the radiography apparatus according to the eighth aspect or the ninth aspect citing the eighth aspect, the rotation mechanism may have a rotation shaft that is rotated with the rotation of the arm and the electromagnetic brake may be connected to the rotation shaft.

According to the above-mentioned configuration, the components of the rotation mechanism and the electromagnetic brake are connected to each other to reduce the size of each mechanism, as compared to a case in which the rotation mechanism and the electromagnetic brake are independently configured.

According to an eleventh aspect of the present disclosure, in the radiography apparatus according to the ninth aspect or the tenth aspect, the arm may have an arc shape in a side view. The rotation mechanism may include a first rotation mechanism comprising a track portion that is provided in the support portion and supports the arm so as to be movable along the arc shape, a fitting portion that is formed in an outer peripheral portion of the arm and is fitted to the track portion, and a first rotation shaft as the rotation shaft. The arm may be moved with respect to the track portion to be orbitally rotated about a center of the arc shape as a rotation center.

According to the above-mentioned configuration, since the arm can be orbitally rotated along the arc shape, the irradiation unit and the image receiving unit can be rotated about the body axis of the subject.

According to a twelfth aspect of the present disclosure, in the radiography apparatus according to the eleventh aspect citing the ninth aspect, the rotation mechanism may further include a belt that has one end fixed to an end of the arm at which the irradiation unit is provided and the other end fixed to an end f the arm at which the image receiving unit is provided. The belt may be wound around the first rotation shaft.

According to the above-mentioned configuration, it is possible to operatively associate the components of the rotation mechanism with the components of the friction mechanism even in orbital rotation and to reduce the size of each mechanism, as compared to a case in which the rotation mechanism and the friction mechanism are independently configured.

Further, as a modification example of the orbital rotation mechanism, a rack and pinion system or a system in which a chain and a sprocket are combined are considered instead of the belt. However, in a case in which the belt is used, the weight of the apparatus can be less than that in these systems.

According to a thirteenth aspect of the present disclosure, in the radiography apparatus according to any one of the ninth to twelfth aspects, the rotation mechanism may include a second rotation mechanism comprising a second rotation shaft as the rotation shaft that has one end fixed to the arm and a bearing that is provided in the support portion. The arm may be rotated about the second rotation shaft with respect to the bearing to reverse positions of the irradiation unit and the image receiving unit with respect to the subject.

According to the above-mentioned configuration, since the arm is rotatable about the rotation shaft, it is possible to switch between an overtube posture in which the irradiation unit is disposed above the image receiving unit and an undertube posture in which the irradiation unit is disposed below the image receiving unit.

According to a fourteenth aspect of the present disclosure, the radiography apparatus according to any one of the first to thirteenth aspects may further comprise an operation handle that is provided independently of the arm and is manually operated to input an operation force for displacing the arm to the displacement mechanism.

According to the above-mentioned configuration, the operation handle makes it possible to operate the arm, without directly operating the arm. Further, since the arm is displaced through the displacement mechanism, the amount of displacement of the arm can be adjusted more easily than that in a case in which the arm is directly operated.

That is, the gear ratio of the displacement mechanism can be set to adjust the relationship between the amount of operation of the operation handle and the amount of displacement of the arm. Therefore, the setting of reducing the amount of displacement of the arm with respect to the amount of displacement of the operation handle is relatively simple. The operation handle makes it easy to finely adjust the amount of displacement of the arm.

In many cases, the arm that holds the irradiation unit and the image receiving unit is used during surgery. Since the operation handle is provided independently of the arm, it is possible to separate an operation part operated by the operator from an operation part operated by the assistant. Therefore, the following method can also be used: the assistant rotates the arm while avoiding the operation part contaminated by contact with the operator.

According to the technology of the present disclosure, it is possible to change a load due to the manual operation force of the arm.

BRIEF DESCRIPTION OF THE DRAWINGS

Exemplary embodiments according to the technique of the present disclosure will be described in detail based on the following figures, wherein:

FIG. 20B is a cross-sectional view illustrating the image receiving unit illustrated in FIG. 20A.

DETAILED DESCRIPTION

Figure 1:
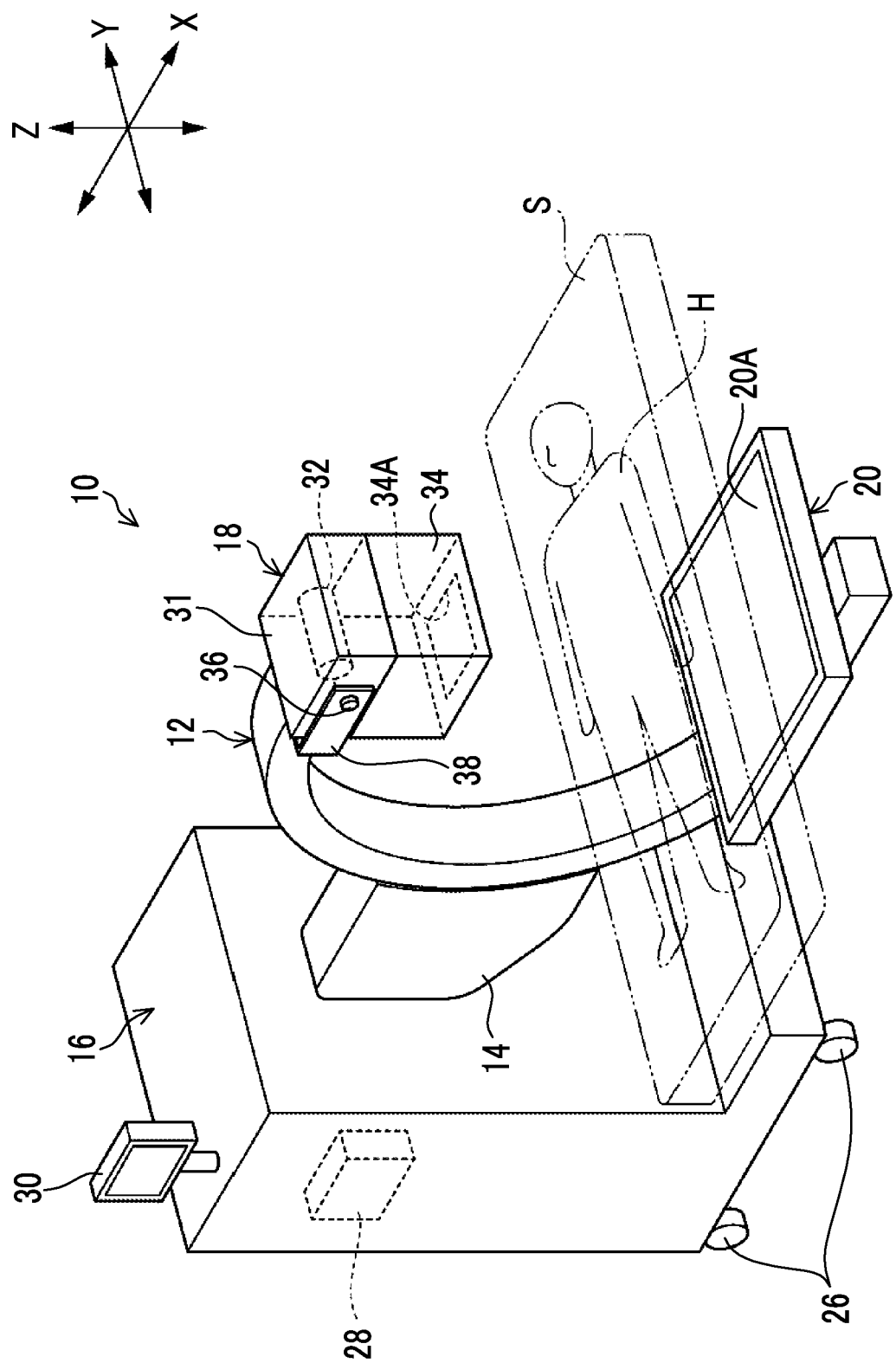
FIG. 1 is an overall perspective view illustrating a radiography apparatus according to a first embodiment.

Hereinafter, radiography apparatuses according to first to third embodiments of the present disclosure will be sequentially described with reference to the drawings. In the drawings, an arrow X indicates the front-rear direction of the radiography apparatus, an arrow Y indicates the width direction of the radiography apparatus, and an arrow Z indicates the vertical direction.

First Embodiment

First, a radiography apparatus according to the first embodiment of the present disclosure will be described with reference to FIGS. 1 to 7.

Overall Configuration of Radiography Apparatus

A radiography apparatus 10 according to this embodiment illustrated in FIG. 1 is an apparatus that captures a radiographic image of a subject H. The radiography apparatus 10 can capture, for example, moving images and still images of the subject H. The capture of the moving image is performed, for example, in a case in which a treatment target part of the subject H is displayed as a moving image during surgery (also referred to as fluoroscopy). In the capture of the moving image, for example, the moving image of the subject H is displayed on a monitor (not illustrated) that is provided separately from the radiography apparatus 10. Of course, data of the captured moving image may be stored in a memory of the radiography apparatus 10. In addition, in the case of the capture of the still image, the captured still image may be displayed on the monitor or may be stored in the memory of the radiography apparatus 10.

As illustrated in FIG. 1, the radiography apparatus 10 includes an arm 12 (referred to as a C-arm or the like) having a C-shape (an arc shape) in a side view and a main body 16 to which a connection portion 14 is attached. Hereinafter, it is assumed that the side of the radiography apparatus 10 on which the arm 12 is provided is the front side of the radiography apparatus 10 and the side on which the main body 16 is provided is the rear side of the radiography apparatus 10.

Configuration of Arm

The arm 12 has two ends. An irradiation unit 18 is provided at one end of the arm 12 and an image receiving unit 20 is provided at the other end. The arm 12 can hold the irradiation unit 18 and the image receiving unit 20 in a posture in which they face each other. A space, into which the subject H and a bed S on which the subject H lies supine can be inserted, is ensured between the irradiation unit 18 and the image receiving unit 20. In the following description, in some cases, in a side view of the arm 12 (as viewed from the Y direction in FIG. 1), a direction in which the irradiation unit 18 and the image receiving unit 20 are provided on the basis of the arm 12 is referred to as the front side of the arm 12 and the side of the arm 12 is referred to as the rear side of the arm 12.

Figure 2A:
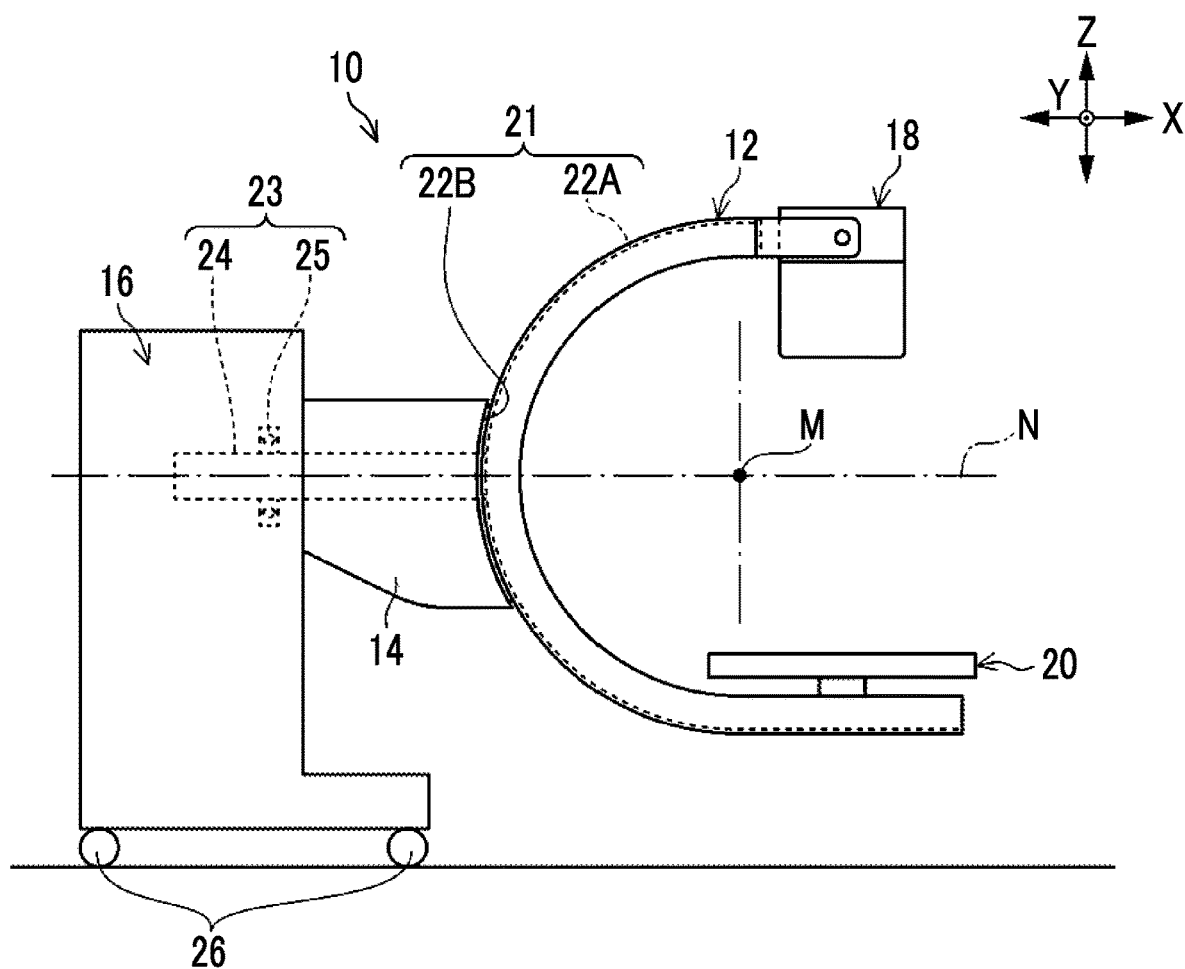
FIG. 2A is a side view illustrating the radiography apparatus according to the first embodiment.

The arm 12 can be rotated by a manual operation. Specifically, as illustrated in FIG. 2A, the arm 12 can be orbitally rotated about an axis line M (an axis line parallel to the Y axis) with respect to the connection portion 14 by a first rotation mechanism 21 which is an example of a displacement mechanism. Further, the arm 12 can be rotated about an axis line N (an axis line parallel to the X-axis) with respect to the main body 16 by a second rotation mechanism 23 which is an example of the displacement mechanism. In this embodiment, the connection portion 14 or the main body 16 corresponds to a "support portion" that supports the arm 12.

The first rotation mechanism 21 comprises a track portion 22B that is provided in the connection portion 14 and a fitting portion 22A that is formed on an outer peripheral surface of the arm 12 and is fitted to the track portion 22B. The first rotation mechanism 21 further comprises a pulley shaft 48 as a first rotation shaft, which will be described below, and a belt 46.

Figure 5:
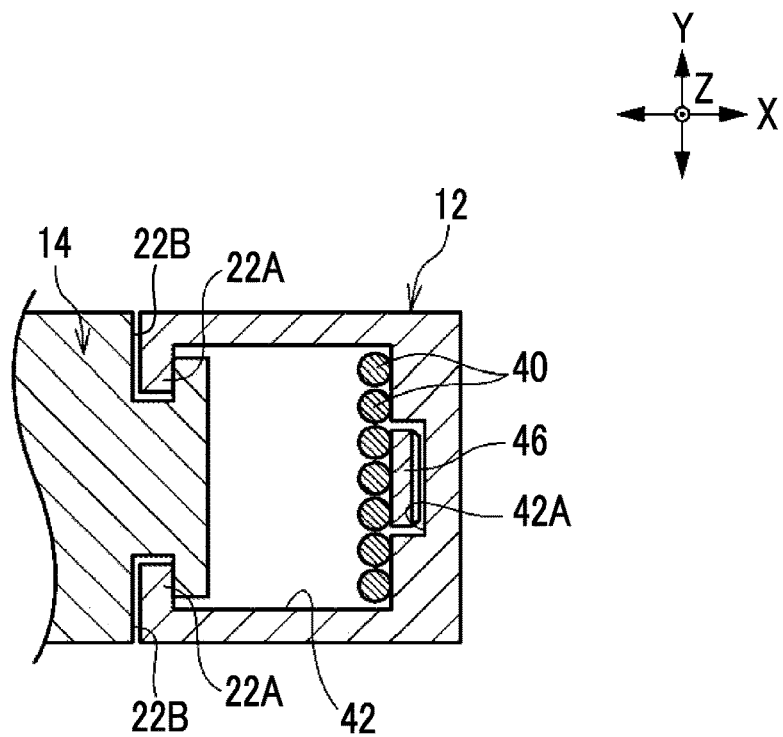
FIG. 5 is a cross-sectional view taken along the line A-A of FIG. 4.

The fitting portion 22A has an arc shape following the shape of the arm 12. The track portion 22B has an arc shape that has the same radius as the arc of the arm 12 and supports the arm 12 so as to be movable along the arc shape. As illustrated in FIG. 5, the track portion 22B has, for example, a groove shape and the fitting portion 22A having a convex shape is fitted to the track portion 22B. A roller (not illustrated) that assists the sliding of the fitting portion 22A with respect to the track portion 22B is interposed between the track portion 22B and the fitting portion 22A.

The fitting portion 22A formed in the arm 12 slides along the track portion 22B formed in the connection portion 14 such that the arm 12 can be orbitally rotated about the axis line M at the center of the arc of the arm 12 as a rotation center with respect to the connection portion 14 and the main body 16.

Figure 2B:
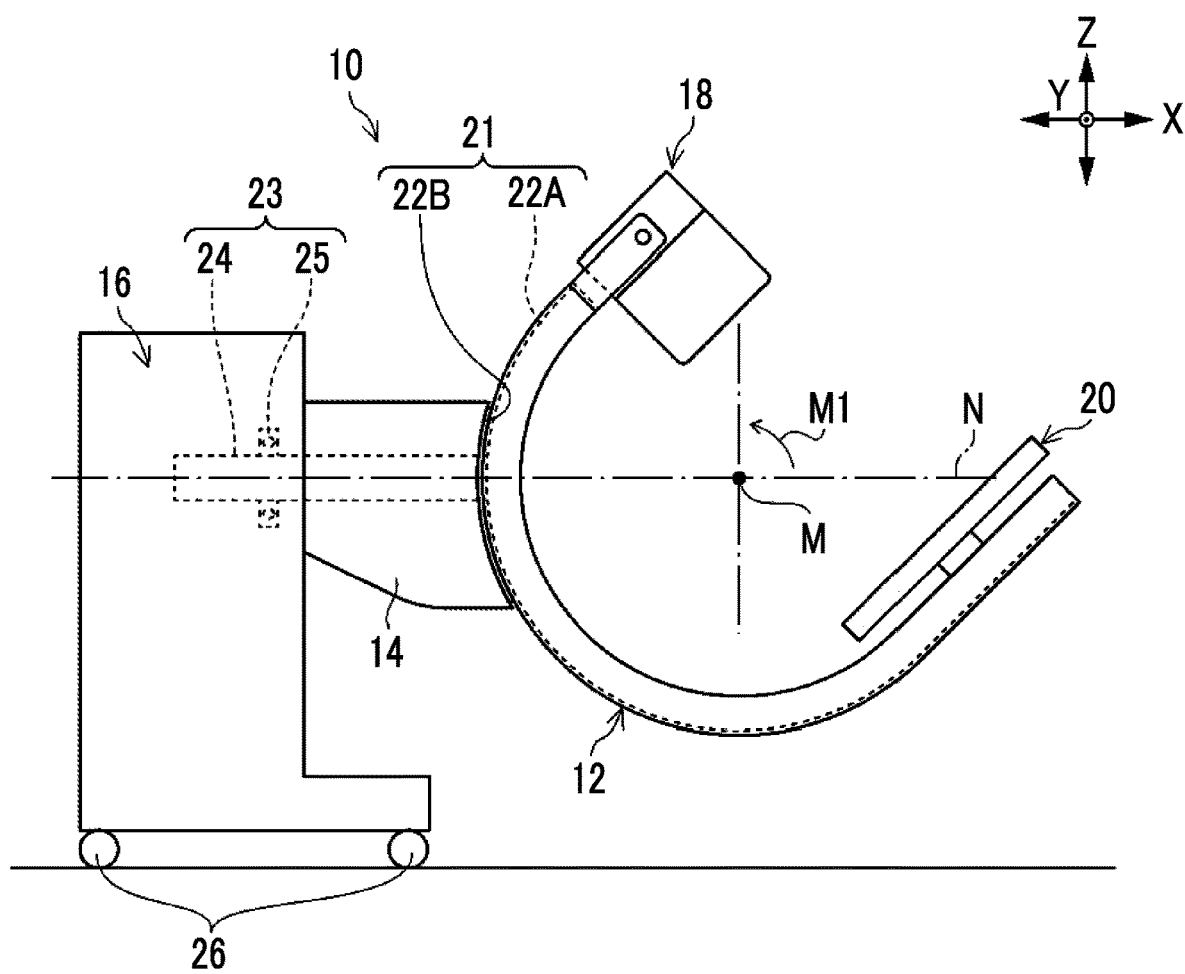
FIG. 2B is a side view illustrating a state in which an arm of the radiography apparatus illustrated in FIG. 2A is rotated in the direction of an arrow M1.
Figure 2C:
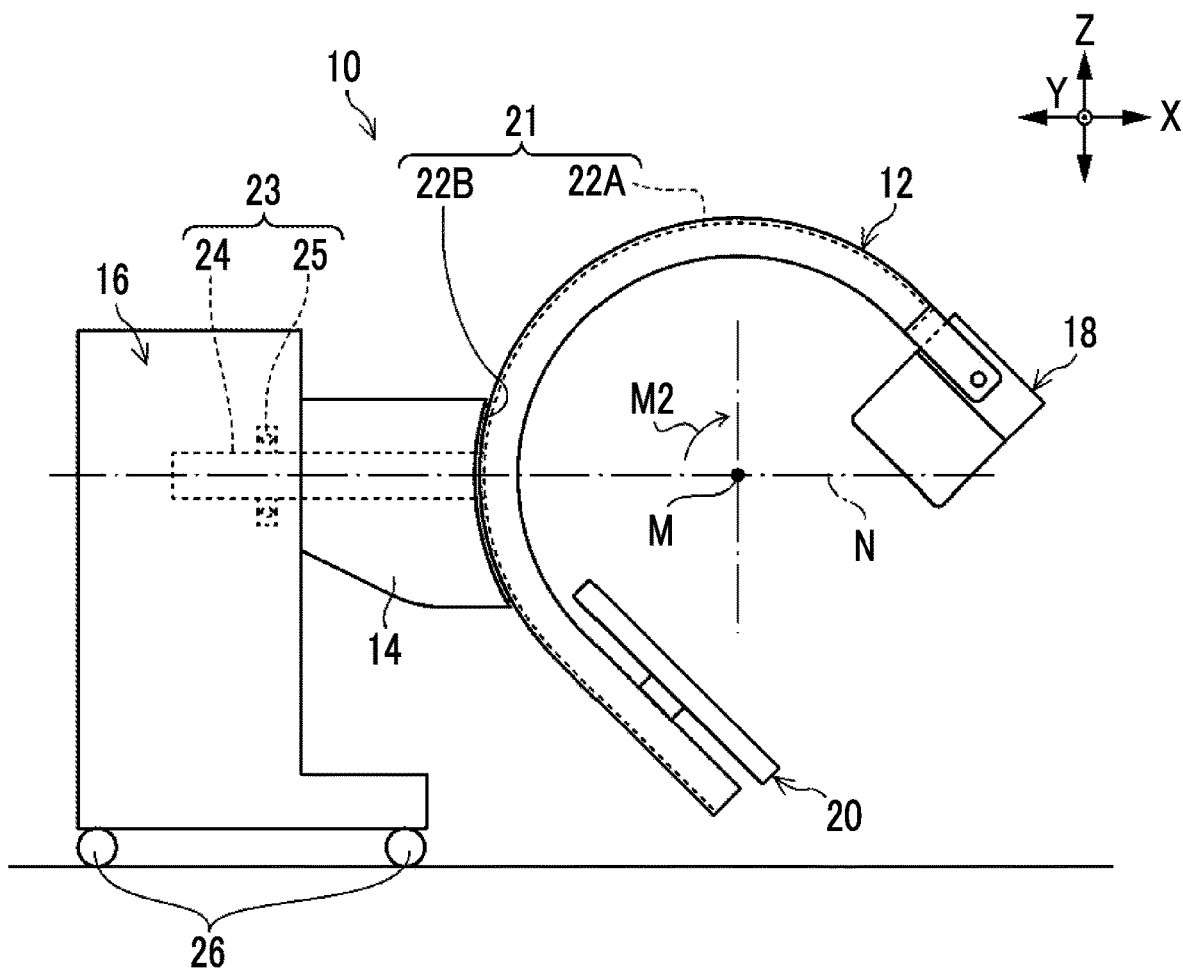
FIG. 2C is a side view illustrating a state in which the arm of the radiography apparatus illustrated in FIG. 2A is rotated in the direction of an arrow M2.

That is, as illustrated in FIGS. 2B and 2C, it is possible to orbitally rotate the arm 12 about the axis line M in the direction of an arrow M1 (counterclockwise in FIG. 2B) and the direction of an arrow M2 (clockwise in FIG. 2C). Therefore, it is possible to rotate the irradiation unit 18 and the image receiving unit 20 provided at both ends of the arm 12 about the body axis (an axis parallel to the Y axis) of the subject H (see FIG. 1).

As illustrated in FIG. 2A, the second rotation mechanism 23 comprises a support shaft 24 as a second rotation shaft, one end of which is fixed to the arm 12, and a bearing 25 which is provided in the main body 16. The support shaft 24 extends in the front-rear direction (X direction) of the radiography apparatus 10 and has the other end that is supported by the main body 16 through the bearing 25.

Figure 3A:
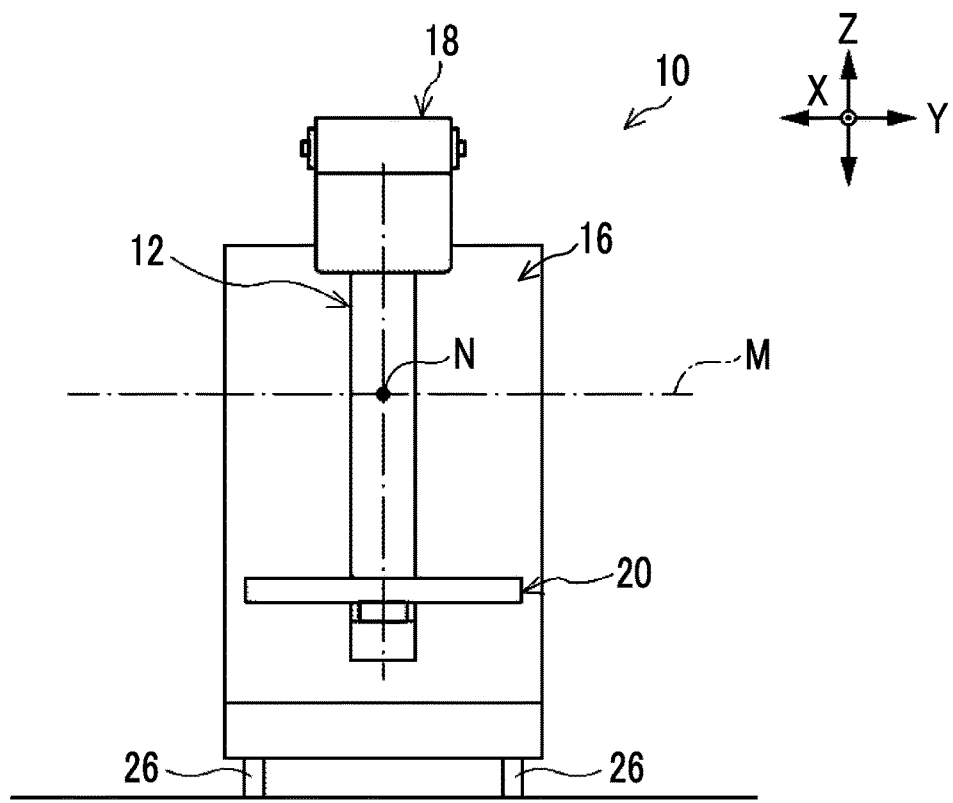
FIG. 3A is a front view illustrating the radiography apparatus according to the first embodiment.
Figure 3B:
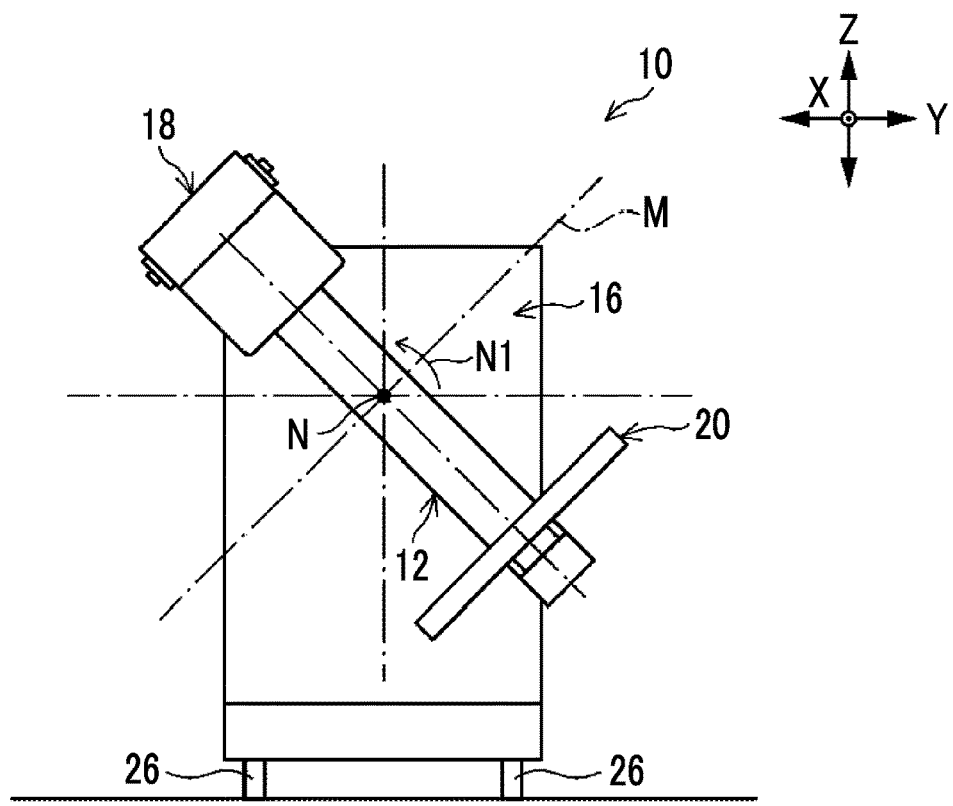
FIG. 3B is a front view illustrating a state in which the arm of the radiography apparatus illustrated in FIG. 3A is rotated in the direction of an arrow N1.
Figure 3C:
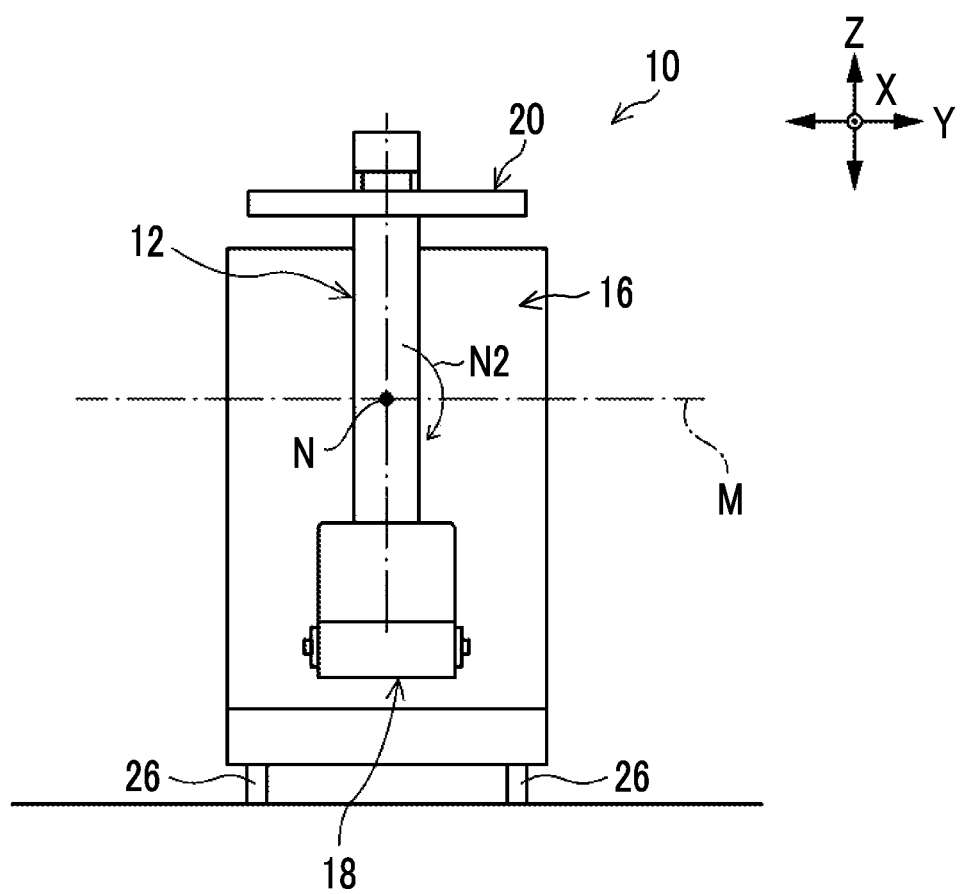
FIG. 3C is a front view illustrating a state in which the arm of the radiography apparatus illustrated in FIG. 3A is rotated 180° in the direction of an arrow N2.

The support shaft 24 is rotated about the axis line N with respect to the bearing 25 such that the arm 12 and the connection portion 14 are rotatable about the axis line N of the support shaft 24 with respect to the main body 16 as illustrated in FIGS. 3A to 3C.

That is, as illustrated in FIGS. 3B and 3C, it is possible to rotate the arm 12 about the axis line N in the direction of an arrow N1 (counterclockwise in FIG. 3B) and the direction of an arrow N2 (clockwise in FIG. 3C). Therefore, it is possible to reverse the positions of the irradiation unit 18 and the image receiving unit 20 provided at both ends of the arm 12 with respect to the subject H (see FIG. 1) in the vertical direction (Z-axis direction).

Here, the posture of the arm 12 in which the irradiation unit 18 is disposed above the image receiving unit 20 as illustrated in FIG. 3A is also referred to as an overtube posture since a radiation tube 32 (see FIG. 1) included in the irradiation unit 18 is located above the subject H. In contrast, the posture of the arm 12 in which the irradiation unit 18 is disposed below the image receiving unit 20 illustrated in FIG. 3C is referred to as an undertube posture since the radiation tube 32 is located below the subject H.

In the overtube posture, it is possible to increase a distance between the irradiation unit 18 and the subject H (see FIG. 1) and thus to capture an image of a relatively wide region, as compared to the undertube posture. Therefore, the overtube posture is mainly used to capture the still image of the subject H. In contrast, in the undertube posture, since the radiation emitted from the irradiation unit 18 is partially shielded by, for example, the bed S, it is possible to reduce the amount of radiation exposure of a surgeon or an operator (not illustrated) around the subject H (see FIG. 1). Therefore, the undertube posture is used for the capture of the moving image of the subject H in which radiation is continuously emitted.

Configuration of Main Body

As illustrated in FIG. 1, a plurality of casters 26 are attached to a lower portion of the main body 16 of the radiography apparatus 10 and the operator can push the radiography apparatus 10 with hands to move the radiography apparatus 10 into, for example, an operating room or a hospital ward. That is, the radiography apparatus 10 according to this embodiment is a mobile type.

Further, the main body 16 includes a control unit 28 that controls each unit of the radiography apparatus 10, such as the irradiation unit 18, and an operation panel 30 that is, for example, a touch panel type. In addition, the main body 16 comprises various switches (not illustrated) including, for example, a power switch of the radiography apparatus 10, a power supply circuit that supplies power to each unit of the radiography apparatus 10, and a battery.

The operation panel 30 functions as an operation unit that inputs an operation command to each unit of the radiography apparatus 10 to operate each unit and a display unit that displays various kinds of information, such as a warning message and a radiographic image output from the image receiving unit 20.

Configuration of Control Unit

The control unit 28 transmits a control signal to the radiation tube 32 of the irradiation unit 18, which will be described below, to control, for example, the tube voltage, tube current, and irradiation time of radiation of the radiation tube 32. The tube voltage is controlled to control the energy of radiation and the tube current and the irradiation time are controlled to control the dose of radiation. In practice, since a high voltage is applied to the radiation tube 32, the control unit 28 controls the radiation tube 32 through a high-voltage generation device (not illustrated). In imaging, imaging conditions including, for example, the tube voltage, the tube current, and the irradiation time are set through the operation panel 30. The control unit 28 operates the irradiation unit 18 on the basis of the set imaging conditions.

The control unit 28 directs the irradiation unit 18 to perform moving image capture irradiation in which the irradiation unit 18 continuously emits radiation such that a moving image of the subject H can be captured. In a case in which a moving image is captured, the control unit 28 operates a detector of the image receiving unit 20 which will be described below in synchronization with the moving image capture irradiation by the irradiation unit 18. In the case of the capture of a moving image, basically, the irradiation time is not set as the imaging condition and commands to start and end the capture of a moving image are input through the operation panel 30. In a case in which the command to start the capture of a moving image is input, the control unit 28 directs the irradiation unit 18 to start the emission of radiation under preset imaging conditions.

In the capture of a moving image, the detector repeats an image detection operation at a preset frame rate while the moving image capture irradiation is performed. The image output by the detector is transmitted to the control unit 28. The control unit 28 sequentially outputs the received images to a monitor (not illustrated). Therefore, the moving image of the subject H is displayed on the monitor.

In addition, the control unit 28 directs the irradiation unit 18 to perform still image capture irradiation in which the irradiation unit 18 emits radiation for a shorter time than in the moving image capture irradiation such that a still image of the subject H can be captured.

In the capture of a still image, the control unit 28 operates the detector of the image receiving unit 20 in synchronization with the irradiation timing in the still image capture irradiation by the irradiation unit 18. For example, a command to capture a still image is input through an irradiation switch (not illustrated) that is connected to the control unit 28. In the capture of a still image, the irradiation time is, for example, in the order of several tens of milliseconds to several hundreds of milliseconds. In a case in which a command to capture a still image is input, the control unit 28 operates the irradiation unit 18 on the basis of preset imaging conditions. In the capture of a still image, since the irradiation time is set in the imaging conditions, the irradiation by the irradiation unit 18 ends in a case in which the set irradiation time elapses.

In a case in which the irradiation ends, the detector starts to output the detected image. The image output by the detector is transmitted to the control unit 28. The control unit 28 stores data of the still image in a memory (not illustrated). Then, the stored still image is displayed on the monitor (not illustrated). Therefore, the still image of the subject H is displayed on the monitor. Further, the still image may be displayed on the operation panel 30 in order to check the captured still image immediately after imaging.

Configuration of Irradiation Unit

The irradiation unit 18 comprises a radiation source 31 and an irradiation field limiter 34. The radiation source 31 comprises the radiation tube 32 that generates radiation. The radiation is, for example, X-rays. The radiation tube 32 generates radiation by colliding electrons generated from a cathode with a target (anode). The position where the electrons collide with the target is a focus where radiation is emitted.

The irradiation field limiter 34 is provided below the radiation source 31. The irradiation field limiter 34 (also referred to as a collimator or the like) has a rectangular irradiation opening 34A. The radiation generated by the radiation tube 32 is emitted to the subject H through the irradiation opening 34A. The irradiation field limiter 34 can adjust the opening area of the irradiation opening 34A. The irradiation field limiter 34 has, for example, four shielding plates (not illustrated) that shield radiation. In each of the four shielding plates, each side corresponds to each side of the irradiation opening 34A and defines the irradiation opening 34A. The position of the shielding plates is changed to adjust the opening area of the irradiation opening 34A and the irradiation field of the radiation emitted from the irradiation unit 18 is changed.

Further, the irradiation unit 18 can be rotated about an axis line of a rotation shaft 36 that extends in the width direction of the radiography apparatus 10 (the Y direction in FIG. 1) as a rotation center with respect to the arm 12. Specifically, a pair of attachment plates 38 (one attachment plate is illustrated in FIG. 1) are fixed to one end of the arm 12.

The pair of attachment plates 38 are disposed such that both sides of the irradiation unit 18 in the width direction are interposed therebetween and are connected to both side surfaces of the irradiation unit 18 in the width direction. The rotation shafts 36 are provided on each of the side surfaces of the irradiation unit 18 facing the attachment plates 38 so as to protrude. The rotation shafts 36 are supported by the pair of attachment plates 38 through bearings (not illustrated). Therefore, the irradiation unit 18 can be rotated about the axis line of the rotation shaft 36 as the rotation center with respect to the attachment plates 38 and the orientation of the irradiation opening 34A of the irradiation unit 18 can be changed in the front-rear direction of the arm 12. The orientation of the irradiation opening 34A is changed to change the irradiation direction of radiation.

The irradiation unit 18 is connected to one end of each of a plurality of cables 40 including a signal line for transmitting a control signal and a power line for supplying power. As illustrated in FIG. 5, the cables 40 are provided in a hollow portion 42 that is formed in the arm 12 and extend along the arm 12. The other end of the cable 40 is connected to, for example, the control unit 28 and a power supply circuit (not illustrated) of the main body 16 illustrated in FIG. 1.

Configuration of Image Receiving Unit

As illustrated in FIG. 1, the image receiving unit 20 is provided at the other end of the arm 12 which is a position facing the irradiation unit 18. The image receiving unit 20 is configured by providing the detector in a housing fixed to the arm 12 so as not to be detachable from the housing. The image receiving unit 20 has an image receiving surface 20A that receives the radiation which has been emitted from the irradiation unit 18 and then transmitted through the subject H. The radiation carrying the information of the subject H is incident on the image receiving surface 20A.

The detector is, for example, a flat panel detector (FPD) of a digital radiography (DR) type. The FPD has a detection surface in which a plurality of pixels are two-dimensionally arranged and a thin film transistor (TFT) panel (not illustrated) for driving the pixels. Radiation is incident on the detection surface of the detector through the image receiving surface 20A. The detector converts the incident radiation into an electric signal and outputs a radiographic image indicating the subject H on the basis of the converted electric signal. For example, the detector is an indirect conversion type that converts radiation into visible light using a scintillator and converts the converted visible light into an electric signal. In addition, the detector may be a direct conversion type that directly converts radiation into an electric signal. Further, the image receiving unit 20 may have, for example, a configuration in which an image intensifier (I.I) and a camera are combined other than the configuration using the FPD.

Further, the image receiving unit 20 is connected to, for example, the control unit 28 and the power supply circuit (not illustrated) of the main body 16 by a cable (not illustrated) including a signal line for transmitting a control signal and a power line for supplying power.

Configuration of Friction Mechanism

Figure 4:
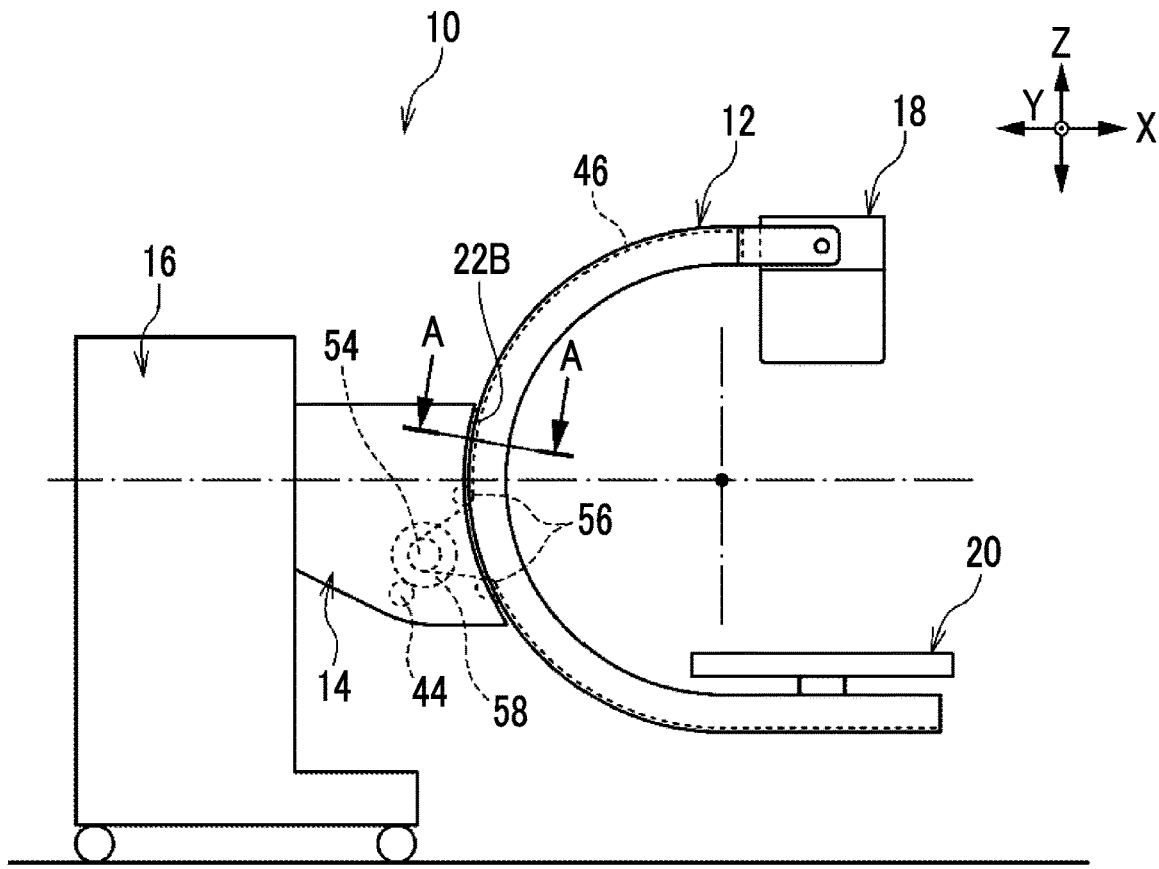
FIG. 4 is an overall side view illustrating a friction mechanism of the radiography apparatus according to the first embodiment.

As illustrated in FIG. 4, the connection portion 14 of the radiography apparatus 10 is provided with a friction mechanism 44 that applies a frictional force to the arm 12 in a direction opposite to the direction in which the arm 12 is displaced.

Specifically, both ends of the belt 46 forming the first rotation mechanism 21 are fixed to both ends of the arm 12, respectively. The arm 12 is a hollow cylindrical body. As illustrated in FIG. 5, the belt 46 and the cables 40 are provided in the hollow portion 42 of the arm 12. In the hollow portion 42, a groove 42A that extends along the arc of the arm 12 is formed in the front inner surface of the arm 12. The belt 46 extends along the arc of the arm 12 while being accommodated in the groove 42A. Therefore, it is possible to suppress interference between the cables 40 and the belt 46 in the hollow portion 42 of the arm 12.

Figure 6:
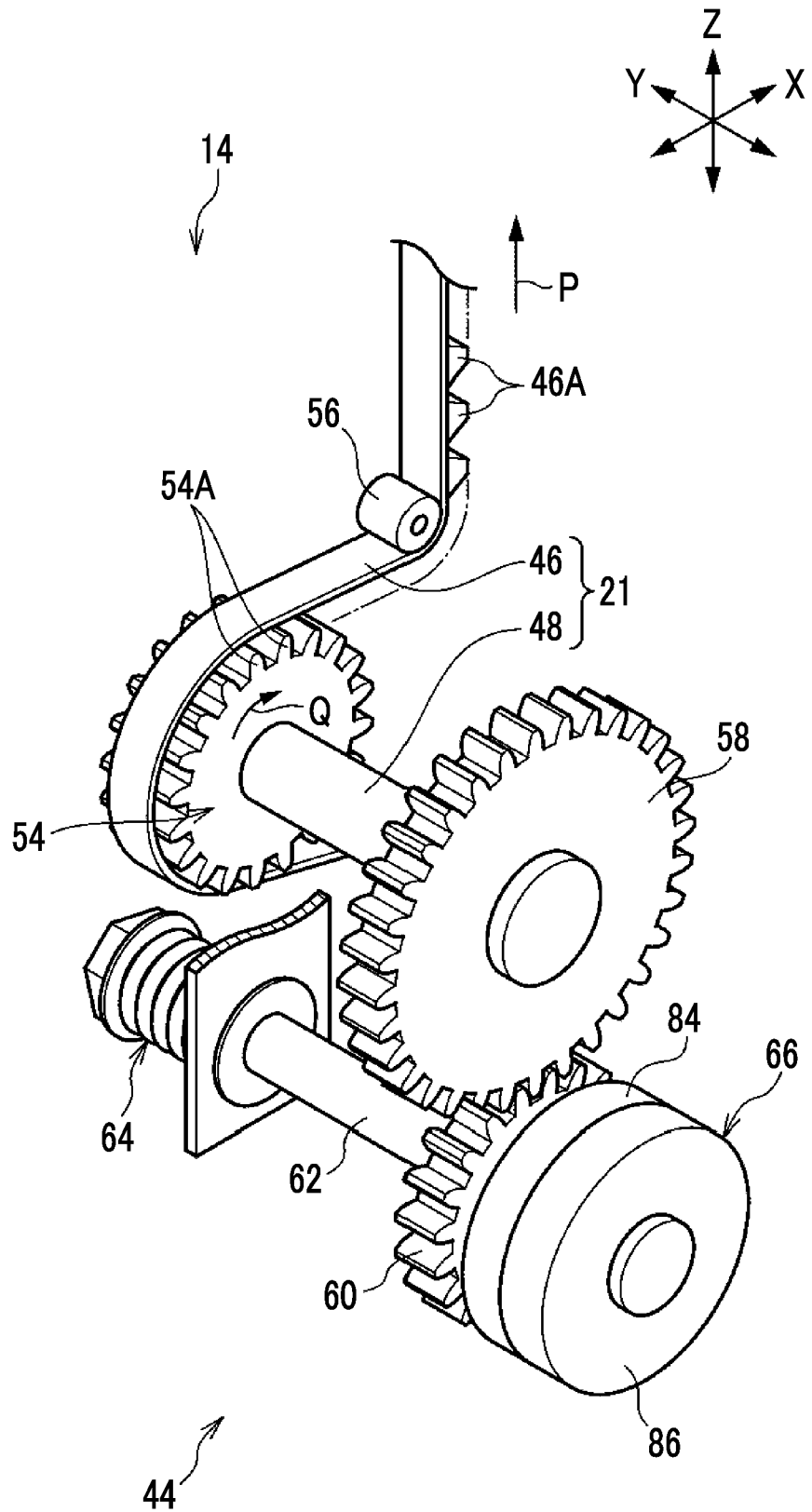
FIG. 6 is a perspective view illustrating the friction mechanism of the radiography apparatus according to the first embodiment.
Figure 7:
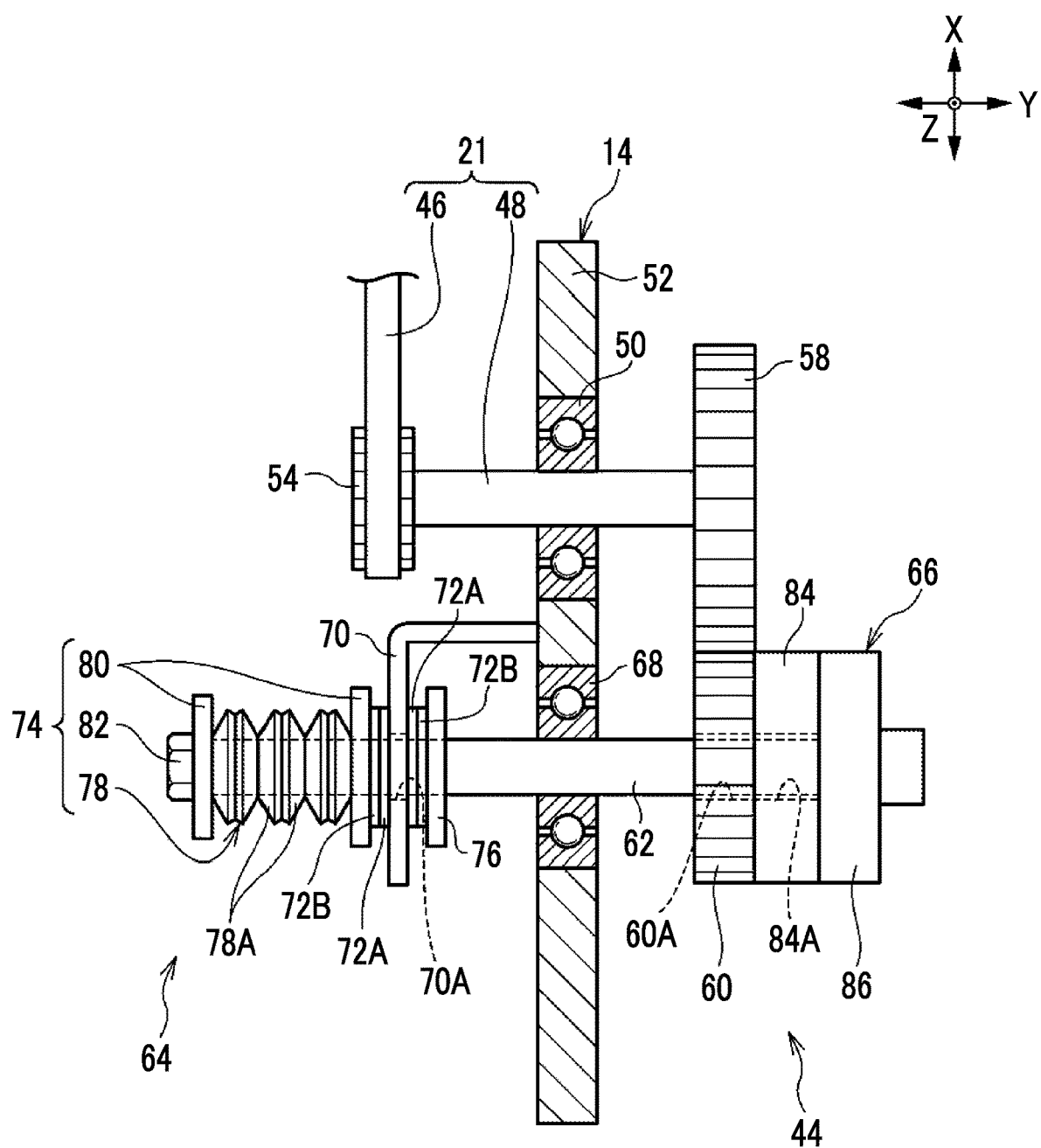
FIG. 7 is a plan view illustrating the friction mechanism illustrated in FIG. 6.

As illustrated in FIGS. 6 and 7, the connection portion 14 is provided with the pulley shaft 48 forming the first rotation mechanism 21. As illustrated in FIG. 7, the pulley shaft 48 is supported by a frame 52 of the connection portion 14 through a bearing portion 50 so as to be rotatable. A pulley 54 is fixed to the pulley shaft 48 so as to be coaxially rotatable and the belt 46 is wound around the pulley 54.

As illustrated in FIG. 6, the belt 46 is a timing belt having a plurality of teeth 46A formed thereon. The pulley 54 is a timing pulley having a plurality of grooves 54A formed in an outer peripheral surface. The teeth 46A of the belt 46 are engaged with the grooves 54A of the pulley 54 such that the belt 46 and the pulley 54 are operatively associated with each other.

Further, as illustrated in FIG. 4, idlers 56 are provided above and below the pulley 54 in the vertical direction (Z direction) in the connection portion 14, respectively. The belt 46 is guided by a pair of idlers 56 while being kept at a predetermined tension and is wound around the pulley 54.

In a case in which the arm 12 is orbitally rotated with respect to the track portion 22B, the belt 46 follows the movement of the arm 12. For example, in a case in which one end of the arm 12 is moved in a direction in which it becomes further away from the connection portion 14 (track portion 22B), the belt 46 is moved in the direction of an arrow P in FIG. 6, that is, in a direction in which the one end becomes further away from the connection portion 14. In this case, the pulley 54 engaged with the belt 46 is also rotated in the direction of an arrow Q (clockwise in FIG. 6) following the movement of the belt 46.

A first gear 58 is fixed to the pulley shaft 48 so as to be rotatable coaxially with the pulley 54. A second gear 60 is engaged with the first gear 58 and the friction mechanism 44 is connected to the second gear 60. The friction mechanism 44 includes a friction shaft 62, a frictional force generation unit 64 that is attached to the friction shaft 62 and generates a frictional force, and a clutch 66 that switches connection and disconnection between the pulley shaft 48 and the friction shaft 62.

As illustrated in FIG. 7, the friction shaft 62 is supported by the frame 52 of the connection portion 14 through a bearing 68 so as to be rotatable. The friction shaft 62 is inserted into a shaft hole 70A that is formed in a side plate 70. The side plate 70 is fixed to the frame 52 at a distance from the frame 52 in the axial direction of the friction shaft 62 (the Y direction in FIG. 7).

The frictional force generation unit 64 comprises two sets of friction plates 72A and 72B that generate a frictional force using contact between friction surfaces, and a biasing portion 74 that biases the friction plates 72A and 72B in a direction in which the friction surfaces are pressed. The two sets of friction plates 72A and 72B are provided on both end surfaces of the side plate 70 in the axial direction of the friction shaft 62, respectively.

A shaft holes (not illustrated) is formed in each of the friction plates 72A and 72B. The friction shaft 62 is inserted into the shaft holes such that the friction plates 72A and 72B are attached so as to be movable in the axial direction of the friction shaft 62. The movement of one set of friction plates 72A and 72B, which is disposed between the side plate 70 and the frame 52, in the axial direction of the friction shaft 62 is regulated by a regulation plate 76 that is fixed to the friction shaft 62.

The friction plate 72A that comes into contact with the end surface of the side plate 70 is fixed by a rotation stopper (not illustrated), and is a fixed friction plate that is not rotated regardless of the rotation of the friction shaft 62. In contrast, the friction plate 72B that is provided outside the friction plate 72A (fixed friction plate) in the axial direction of the friction shaft 62 with respect to the side plate 70 is a rotary friction plate that is rotated as the friction shaft 62 is rotated.

The biasing portion 74 is provided between the side plate 70 and one end of the friction shaft 62 in the axial direction. The biasing portion 74 comprises a disc spring unit 78, a pair of buffer plates 80, and a nut 82 that is provided at one end of the friction shaft 62 in the axial direction.

The disc spring unit 78 includes a plurality of disc springs 78A. The disc spring 78A is a disk-shaped spring that has one convex surface and the other concave surface. The plurality of disc springs 78A are arranged along the axial direction of the friction shaft 62 so as to be stacked.

Further, each of the buffer plates 80 is disposed outside the disc spring units 78 in the axial direction of the friction shaft 62. One buffer plate 80 is disposed between the disc spring unit 78 and the friction plate 72B. The other buffer plate 80 is disposed between the disc spring unit 78 and the nut 82. A shaft hole (not illustrated) is formed in each of the buffer plate 80 and the disc spring 78A. The friction shaft 62 is inserted into the shaft holes such that the buffer plate 80 and the disc spring 78A are attached so as to be movable in the axial direction of the friction shaft 62.

In a case in which the nut 82 is tightened with the end surface of the disc spring unit 78 in contact with one buffer plate 80, the disc spring unit 78 is moved in the direction in which the one buffer plate 80 is pressed. In a case in which the disc spring unit 78 is moved, a pressing force is applied to each set of the friction plates 72A and 72B through the buffer plate 80. In a case in which the nut 82 is further tightened and the disc spring unit 78 reaches a movement limit, the disc spring 78A is elastically deformed and the disc spring unit 78 contracts in the axial direction of the friction shaft 62. The disc spring unit 78 biases the friction surfaces of the friction plates 72A and 72B in a direction in which they are pressed against each other on the basis of elasticity.

As such, the operation of the biasing portion 74 causes the friction surfaces of the friction plates 72A and 72B to come into contact with each other and a normal force is generated on the friction surfaces. Therefore, in a case in which the friction shaft 62 is rotated, a frictional force acts on the friction surfaces of the friction plates 72A and 72B in a direction opposite to a rotation direction of the friction shaft 62.

The clutch 66 is attached to the other end of the friction shaft 62 in the axial direction. In this embodiment, the clutch 66 is an electromagnetic clutch and includes a housing 84 having an electromagnet (not illustrated) provided therein and a shaft fixing portion 86 fixed to the friction shaft 62. The housing 84 and the shaft fixing portion 86 are separated from each other. Further, a biasing member (not illustrated) that biases the housing 84 and the shaft fixing portion 86 in the direction in which they become further away from each other is provided between the housing 84 and the shaft fixing portion 86.

The housing 84 is fixed to the second gear 60. Shaft holes 60A and 84A through which the friction shaft 62 is inserted are formed in the housing 84 and the second gear 60, respectively. A gap is formed between the outer peripheral surface of the friction shaft 62 and the inner peripheral surfaces of the shaft holes 60A and 84A. That is, the housing 84 and the second gear 60 are not connected to the friction shaft 62.

The clutch 66 switches connection and disconnection between the second gear 60 and the friction shaft 62 to switch connection and disconnection between the pulley shaft 48 and the friction shaft 62. Specifically, in a case in which the clutch 66 is energized, a magnetic force is generated in the electromagnet provided in the housing 84 and the shaft fixing portion 86 is attracted to the electromagnet against the biasing force of the biasing member (not illustrated). Therefore, the housing 84 and the shaft fixing portion 86 are closely connected.

In a case in which the pulley shaft 48 is rotated in a state in which the housing 84 is connected to the shaft fixing portion 86 (corresponding to a first state), the first gear 58, the second gear 60, and the housing 84 of the clutch 66 are rotated with the rotation of the pulley shaft 48. The shaft fixing portion 86 of the clutch 66 connected to the housing 84 and the friction shaft 62 to which the shaft fixing portion 86 is fixed are also rotated with the rotation of the pulley shaft 48.

As described above, since the frictional force in the direction opposite to the rotation direction acts on the friction shaft 62, the friction shaft 62 is rotated with the rotation of the pulley shaft 48 and the frictional force acts on the pulley shaft 48 in the direction opposite to the rotation direction. The pulley 54 is fixed to the pulley shaft 48 and the belt 46 fixed to both ends of the arm 12 illustrated in FIG. 4 is wound around the pulley 54.

Therefore, a frictional force acts on the pulley shaft 48 in a direction opposite to the rotation direction. In a case in which the arm 12 is orbitally rotated with respect to the track portion 22B (see FIG. 4), a frictional force acts on the arm 12 in a direction opposite to the rotation direction of the arm 12.

In contrast, in a case in which the clutch 66 is de-energized, the housing 84 fixed to the second gear 60 and the shaft fixing portion 86 fixed to the friction shaft 62 are biased by a biasing member (not illustrated) and are separated from each other. Therefore, the housing 84 and the shaft fixing portion 86 are disconnected and the second gear 60 and the friction shaft 62 are disconnected.

In a case in which the pulley shaft 48 is rotated in a state in which the housing 84 and the shaft fixing portion 86 are disconnected (corresponding to a second state), the first gear 58, the second gear 60, and the housing 84 of the clutch 66 are rotated with the rotation of the pulley shaft 48. However, the shaft fixing portion 86 of the clutch 66 and the friction shaft 62 are not rotated. Therefore, the frictional force that acts on the friction shaft 62 in a case in which the pulley shaft 48 is rotated does not act. The frictional force that acts on the arm 12 in a case in which the arm 12 is orbitally rotated is less than that in a case in which the clutch 66 is energized.

The operator operates the operation panel 30 (see FIG. 1) as an operation unit to perform the switching between the first state and the second state of the friction mechanism 44. For example, in a case in which the operator inputs an operation command to switch the friction mechanism 44 to the first state to the operation panel 30, the control unit 28 (see FIG. 1) transmits a driving signal to the clutch 66 to energize the clutch 66. Therefore, the housing 84 and the shaft fixing portion 86 of the clutch 66 are connected to each other to switch the friction mechanism 44 to the first state in which the frictional force acts on the arm 12.

In contrast, in a case in which the operator inputs an operation command to switch the friction mechanism 44 to the second state to the operation panel 30, the control unit 28 (see FIG. 1) de-energizes the clutch 66. Therefore, the housing 84 and the shaft fixing portion 86 of the clutch 66 are disconnected from each other to switch the friction mechanism 44 to the second state in which the frictional force does not act on the arm 12.

Operation and Effect

The radiography apparatus 10 according to this embodiment comprises the first rotation mechanism 21 (an example of the displacement mechanism) that rotates the arm 12 with respect to the connection portion 14 and the friction mechanism 44 that applies a frictional force to the arm 12 in a direction opposite to the direction in which the arm 12 is rotated by the first rotation mechanism 21.

Further, the friction mechanism 44 can be switched between the first state in which a frictional force is applied to the arm 12 in the direction opposite to the direction in which the arm 12 is displaced and the second state in which the frictional force applied to the arm 12 is less than that in the first state. Therefore, the friction mechanism 44 is switched between the first state and the second state to change a load due to the manual operation force of the arm 12 in a case in which the arm 12 is manually rotated.

In particular, according to this embodiment, the arm 12 may not be rotated by an electromotive force, but may be rotated by only a manual operation. Therefore, it is possible to reduce the size and weight of the entire radiography apparatus 10. In many cases, a large-sized radiography apparatus includes a mechanism that electrically displaces the arm. In general, in the large-sized apparatus, the operation force of the arm is controlled through a complicated mechanism such as an electric mechanism.

Here, according to this embodiment, even in a case in which the arm 12 is rotated by only a manual operation to reduce the size and weight of the radiography apparatus 10, the friction mechanism 44 can switch the operation force of the arm 12 with a relatively simple structure. Therefore, the technology of this embodiment is particularly effective for the radiography apparatus 10 with a small size and weight in which the arm 12 is rotated by only a manual operation.

Further, according to this embodiment, the first rotation mechanism 21 has the pulley shaft 48 that is rotated as the arm 12 is rotated. Then, the friction mechanism 44 comprises the friction shaft 62, the frictional force generation unit 64 that is attached to the friction shaft 62 and generates a frictional force, and the clutch 66 that switches connection and disconnection between the pulley shaft 48 and the friction shaft 62.

As described above, the operative association between the components of the first rotation mechanism 21 and the components of the friction mechanism 44 makes it possible to reduce the size of each mechanism, as compared to a case in which the first rotation mechanism 21 and the friction mechanism 44 are independently configured.

In particular, according to this embodiment, the first rotation mechanism 21 has the pulley shaft 48 to which the pulley 54 is fixed and the belt 46 which has both ends fixed to both ends of the arm 12 and is wound around the pulley 54. As such, since the belt 46 fixed to both ends of the arm 12 is wound around the pulley 54 fixed to the pulley shaft 48, it is possible to operatively associate the components of the first rotation mechanism 21 with the components of the friction mechanism 44 even in a case in which the arm 12 is orbitally rotated.

Further, as a modification example of the first rotation mechanism 21, a rack and pinion system or a system in which a chain and a sprocket are combined are considered instead of the belt 46. However, in a case in which the belt 46 is used, the weight of the apparatus can be less than that in these systems.

Further, in addition to the first rotation mechanism 21 and the second rotation mechanism 23, for example, a slide mechanism that slides the arm 12 in the horizontal direction (X direction) with respect to the main body 16 is considered as the displacement mechanism for displacing the arm 12. However, in general, in the operation of rotating the arm 12, a load is less than that in the operation of sliding the arm 12 in the horizontal direction. Therefore, the friction mechanism 44 according to this embodiment which can switch the frictional force is particularly effective in a case in which the friction mechanism 44 is combined with the first rotation mechanism 21 or the second rotation mechanism 23.

That is, it is possible to prevent the arm 12 from being inadvertently rotated by switching the friction mechanism 44 to the first state. On the other hand, it is possible to reduce the load in a case in which the arm 12 is manually rotated by switching the friction mechanism 44 to the second state.

Further, according to this embodiment, the operator operates the operation panel 30 as the operation unit to perform the switching between the first state and the second state by the friction mechanism 44. That is, the operator can optionally switch the frictional force.

Therefore, for example, in a case in which a moving image is captured by the radiography apparatus 10 during surgery, the frictional force is reduced such that positioning is performed with a small force in a preparatory stage before surgery. During surgery, the frictional force is increased to prevent the arm 12 from being inadvertently rotated due to the application of an unintended external force to the arm 12 such as the collision of the operator with the arm 12.

Second Embodiment

Next, a radiography apparatus according to a second embodiment of the present disclosure will be described with reference to FIGS. 8 to 12. In addition, the same configurations as those in the first embodiment are denoted by the same reference numerals and the description thereof will not be repeated. The description is focused on the differences between the first and second embodiments.

Figure 8A:
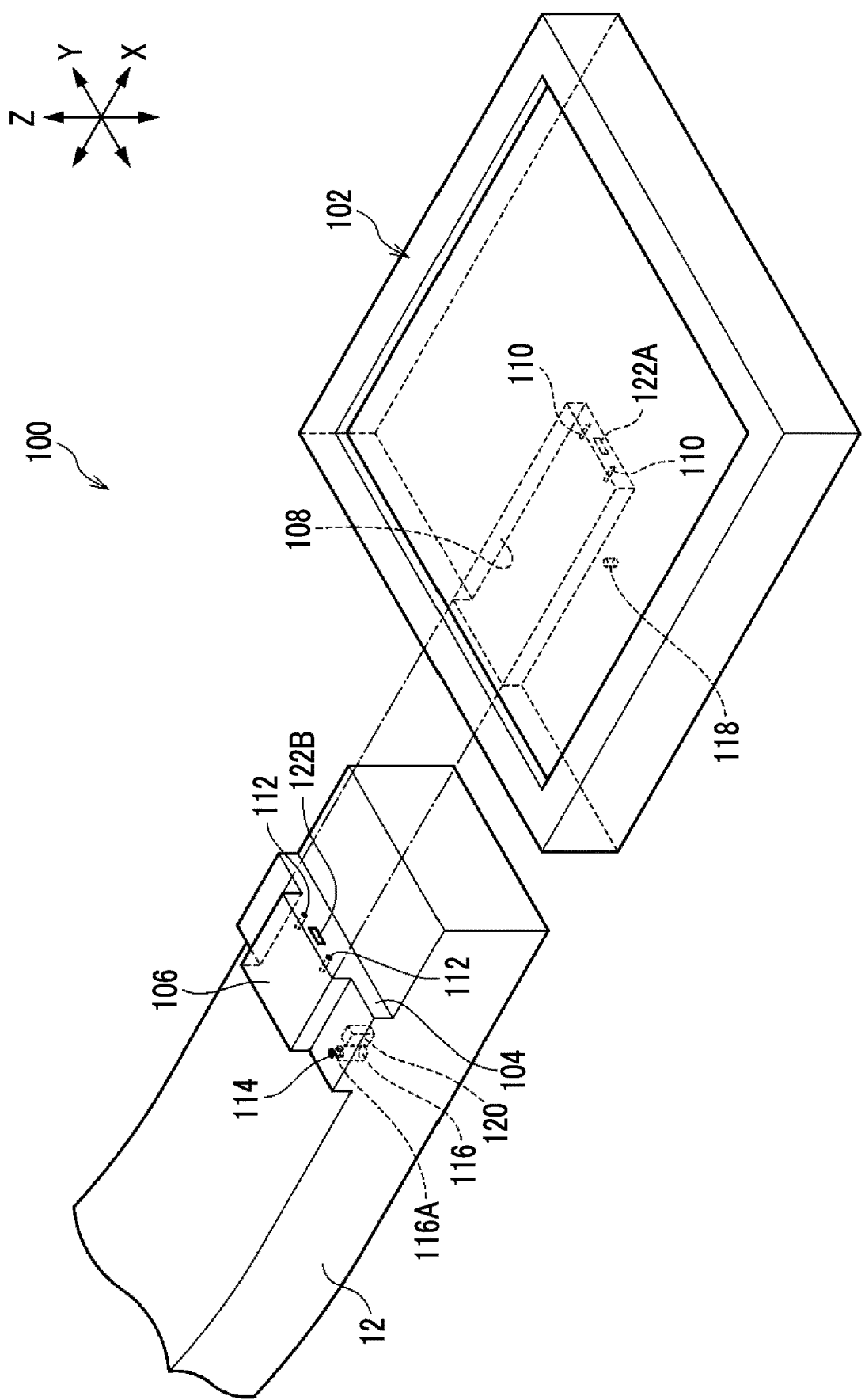
FIG. 8A is a partial perspective view illustrating an image receiving unit of a radiography apparatus according to a second embodiment.

In the radiography apparatus 10 according to the first embodiment, the image receiving unit 20 is fixed to the other end of the arm 12. In contrast, as illustrated in FIG. 8A, in a radiography apparatus 100 according to this embodiment, an image receiving unit 102 is a portable type that is attached to the arm 12 so as to be detachable. In the image receiving unit 102, a detector is provided in a housing so as not to be detachable as in the first embodiment. The portable image receiving unit 102 is called, for example, an electronic cassette.

Configuration of Image Receiving Unit

Specifically, the image receiving unit 102 is attached to a base 104 that is provided at the other end of the arm 12 so as to be detachable. The base 104 is provided on the upper surface of the other end of the arm 12 and a fitting convex portion 106 is provided uprightly on the base 104. Each of the base 104 and the fitting convex portion 106 has a rectangular parallelepiped shape and the width (length in the Y direction) of the fitting convex portion 106 is smaller than the width (length in the Y direction) of the base 104.

The image receiving unit 102 has a flat rectangular parallelepiped shape. A fitting concave portion 108 that is fitted to the fitting convex portion 106 is formed in the lower surface of the image receiving unit 102. The fitting concave portion 108 has a rectangular parallelepiped shape and the length (length in the Y direction in FIG. 8A) of the fitting concave portion 108 in the lateral direction is larger than the width of the fitting convex portion 106 and is smaller than the width of the base 104. Further, the height of the fitting concave portion 108 is substantially equal to the height of the fitting convex portion 106.

In addition, the length (length in the X direction in FIG. 8A) of the fitting concave portion 108 in the longitudinal direction is larger than the length (length in the X direction) of the base 104 and the fitting convex portion 106. One end of the fitting concave portion 108 in the longitudinal direction extends to one side surface of the image receiving unit 102. Since one end of the fitting concave portion 108 is located on one side surface of the image receiving unit 102, a part of one side surface of the image receiving unit 102 is open.

In a case in which the image receiving unit 102 is attached to the arm 12, the image receiving unit 102 is moved in the horizontal direction (X direction) such that the fitting convex portion 106 that is provided uprightly on the base 104 is inserted into the fitting concave portion 108 through the opening formed in one side surface of the image receiving unit 102. Then, the lower surface of the image receiving unit 102 comes into contact with the upper surface of the base 104 in a state in which the fitting convex portion 106 is fitted to the fitting concave portion 108.

Here, a pair of positioning pins 110 that protrude into the fitting concave portion 108 are provided on the other end surface of the fitting concave portion 108 in the longitudinal direction. A pair of pin holes 112 into which the positioning pins 110 are inserted are formed in one side surface of the fitting convex portion 106 which faces the other end surface of the fitting concave portion 108 in the longitudinal direction in a case in which fitting convex portion 106 is fitted to the fitting concave portion 108.

In a case in which the fitting concave portion 108 of the image receiving unit 102 is fitted to the fitting convex portion 106, the pair of positioning pins 110 are inserted into the pair of pin holes 112 such that the image receiving unit 102 is positioned and attached to the base 104, that is, the other end of the arm 12.

A through hole 114 that extends in the vertical direction (Z direction) is formed in the upper surface of the base 104 and a solenoid 116 is provided below the through hole 114 at the other end of the arm 12. An insertion hole 118 having substantially the same diameter as the through hole 114 is formed in the lower surface of the image receiving unit 102. Here, as illustrated in FIG. 8B, the insertion hole 118 of the image receiving unit 102 is formed at a position that communicates with the through hole 114 of the base 104 in a case in which the image receiving unit 102 is positioned and attached to the base 104.

The solenoid 116 comprises a movable iron core 116A that is inserted into the through hole 114. The movable iron core 116A can be expanded and contracted by switching between an energized state and a non-energized state of the solenoid 116.

Figure 8B:
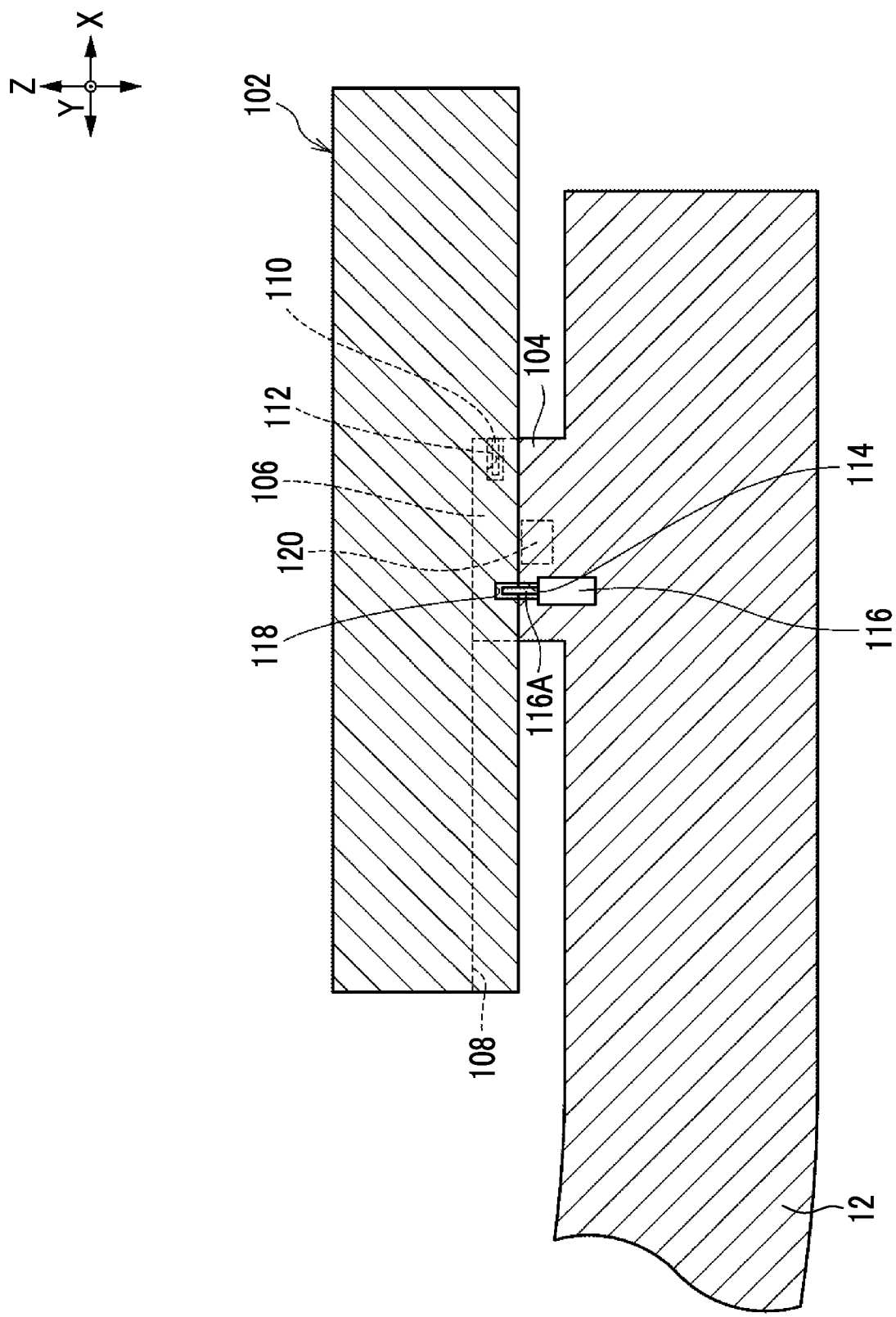
FIG. 8B is a cross-sectional view illustrating the image receiving unit illustrated in FIG. 8A.

Specifically, in a case in which the solenoid 116 is energized, the movable iron core 116A is attracted to the main body of the solenoid 116 and a leading end of the movable iron core 116A is located in the through hole 114 of the base as illustrated in FIG. 8B. In this state, since the movable iron core 116A is not inserted into the insertion hole 118 of the image receiving unit 102, the image receiving unit 102 is attachable to and detachable from the base 104, that is, the arm 12.

In contrast, in a state in which the insertion hole 118 of the image receiving unit 102 and the through hole 114 of the base 104 communicate with each other, that is, in a state in which the image receiving unit 102 is positioned and attached to the other end of the arm 12, the movable iron core 116A can be inserted into the insertion hole 118 of the image receiving unit 102 as illustrated in FIG. 8B.

Therefore, in a case in which the solenoid 116 is de-energized in a state in which the image receiving unit 102 is positioned and attached to the other end of the arm 12, the leading end of the movable iron core 116A is inserted into the insertion hole 118 and reaches the image receiving unit 102. In this state, since the movable iron core 116A of the solenoid 116 is also inserted into the insertion hole 118 of the image receiving unit 102, the detachment of the image receiving unit 102 from the base 104, that is, the arm 12 is regulated. As described above, the solenoid 116 forms an attachment and detachment regulation mechanism that regulates the inadvertent attachment and detachment of the image receiving unit 102 to and from the arm 12 in a state in which the image receiving unit 102 is attached to the arm 12.

Further, the base 104 is provided with a photo sensor 120 as an attachment and detachment detection unit that detects whether or not the image receiving unit 102 is detached from the arm 12. The photo sensor 120 is, for example, a reflective sensor in which a light emitting window through which a light emitting element (not illustrated) emits light and a light receiving window through which a light receiving element (not illustrated) receives light are arranged on the same surface. The photo sensor 120 is provided at a position where the light emitting window and the light receiving window are exposed to the outside in a state in which the image receiving unit 102 is not attached to the base 104 and the image receiving unit 102 covers the light emitting window and the light receiving window in a state in which the image receiving unit 102 is attached to the base 104. For example, the photo sensor 120 according to this example is disposed on the base 104 in a posture facing the upper surface in FIG. 8A.

For example, in a case in which the base 104 is attached to the image receiving unit 102, in the photo sensor 120, the light emitted from the light emitting window is reflected by the image receiving unit 102 such that the amount of light received through the light receiving window increases. In contrast, in a state in which the image receiving unit 102 is detached from the base 104 and is retracted from the front surfaces of the light emitting window and the light receiving window, light is not reflected from the image receiving unit 102 and the amount of light received through the light receiving window is reduced.

As such, the photo sensor 120 detects a change in the light which has been emitted from the light emitting window and then received by the light receiving element to detect whether or not the image receiving unit 102 is detached from the arm 12.

Figure 11:
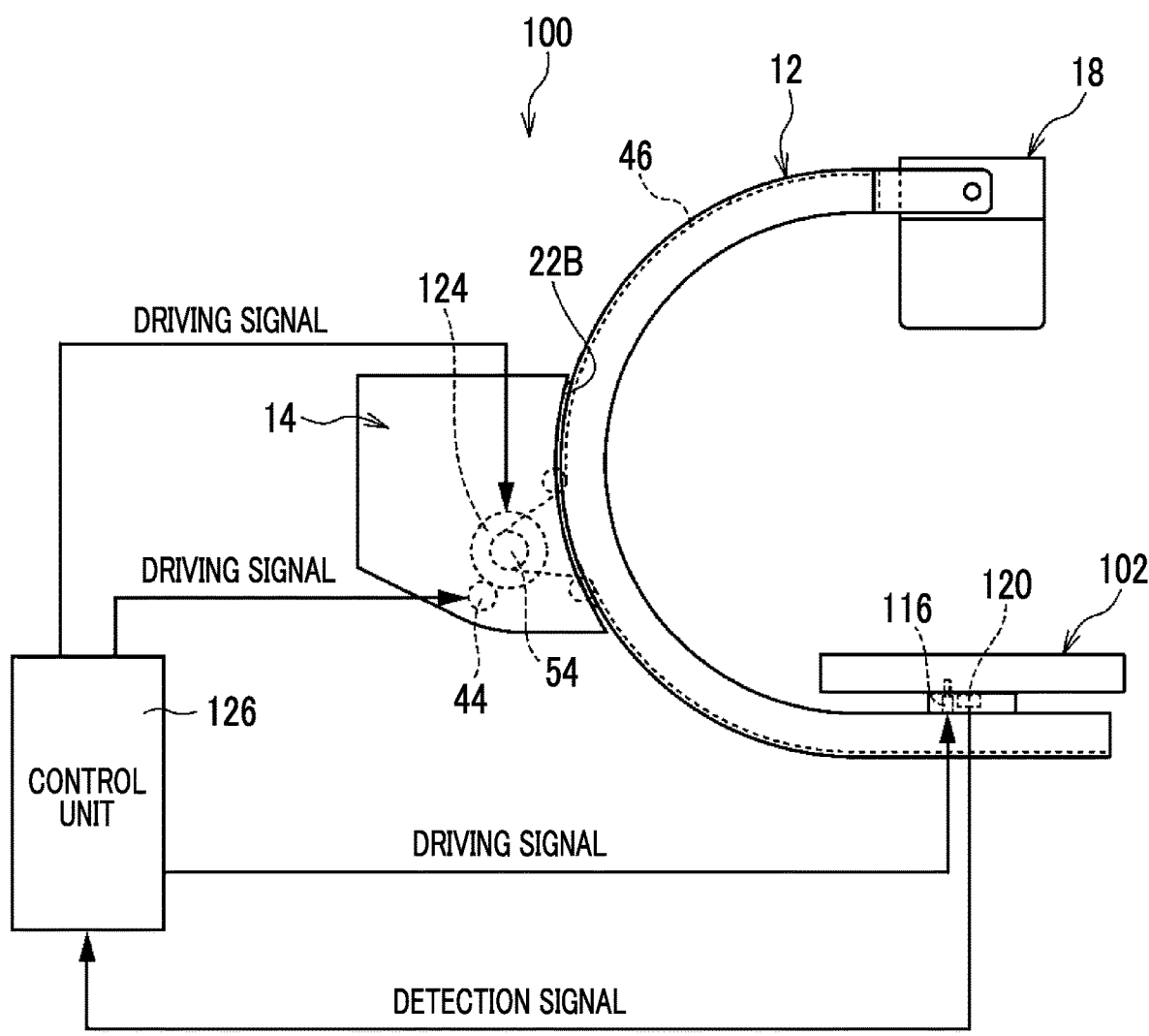
FIG. 11 is a block diagram illustrating a functional configuration of a control unit of the radiography apparatus according to the second embodiment.

The photo sensor 120 outputs an on signal as a detection signal to a control unit 126 illustrated in FIG. 11 in a state in which it is detected that the image receiving unit 20 is attached to the arm 12 and outputs an off signal as the detection signal to the control unit 126 illustrated in FIG. 11 in a state in which it is detected that the image receiving unit 20 is detached from the arm 12.

The portable image receiving unit 102 has, for example, a battery and a wireless communication unit which are not illustrated and can wirelessly communicate with the control unit 126 (see FIG. 11) provided in the main body 16. In a case in which a wireless communication unit is used, the image receiving unit 102 is driven by power from the battery and can be used in a so-called cableless manner. Therefore, the image receiving unit 102 can be used in a state in which it is detached from the arm 12.

In contrast, in a case in which the image receiving unit 102 is attached to the arm 12, a terminal 122A that is provided in the fitting concave portion 108 of the image receiving unit 102 and a terminal 122B that is provided in the fitting convex portion 106 of the arm 12 illustrated in FIG. 8A come into contact with each other and the image receiving unit 102 and the base 104 are electrically connected. Further, the base 104 is connected to, for example, the control unit 126 (see FIG. 11) and a power supply circuit (not illustrated) of the main body 16 by a cable (not illustrated) including a signal line for transmitting a control signal and a power line for supplying power. Therefore, in a state in which the image receiving unit 102 is attached to the arm 12, the image receiving unit 102 is connected to, for example, the control unit 126 and the power supply circuit (not illustrated) through a cable (not illustrated).

Configuration of Connection Portion

Figure 9:
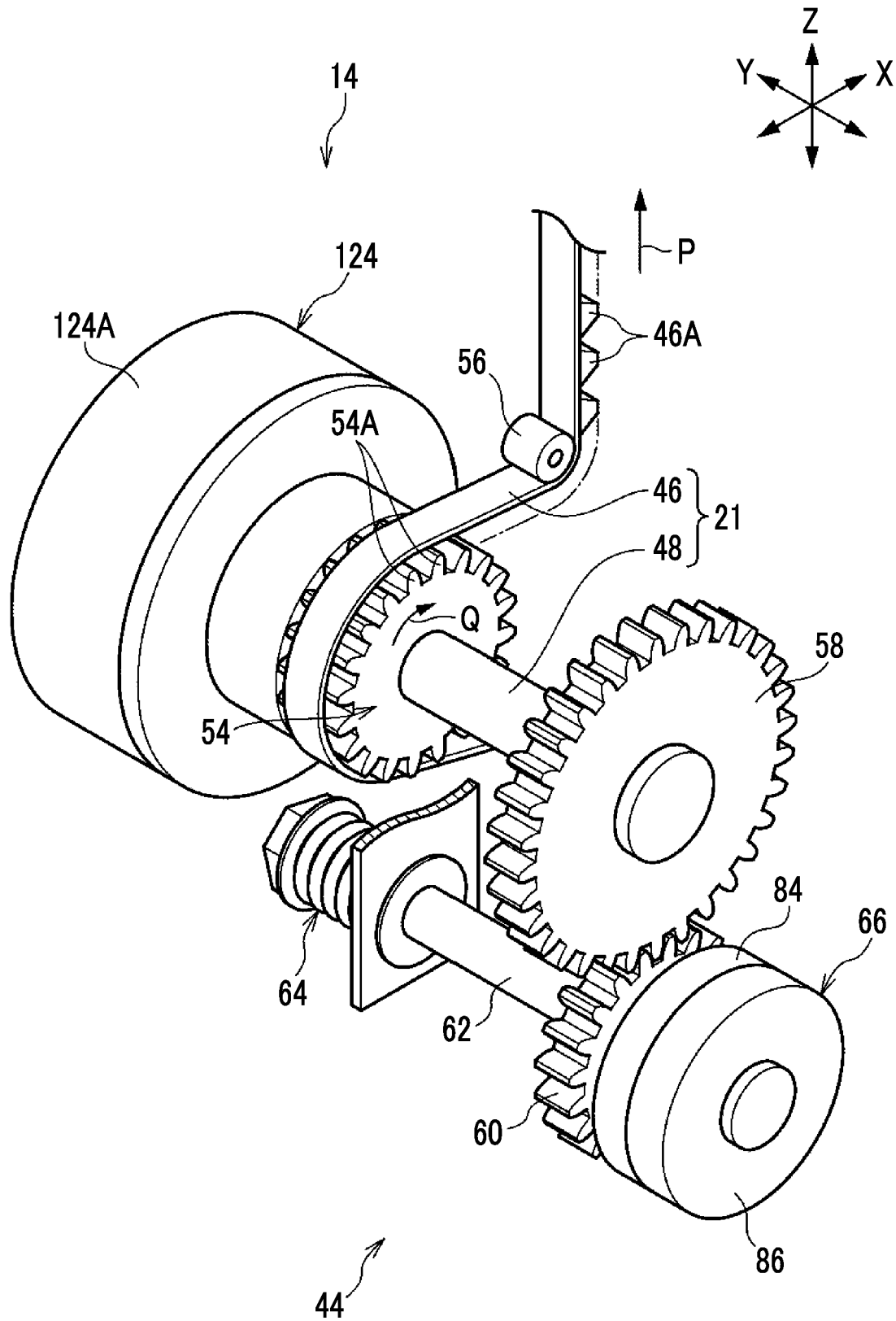
FIG. 9 is a perspective view illustrating a friction mechanism and an electromagnetic brake of the radiography apparatus according to the second embodiment.
Figure 10:
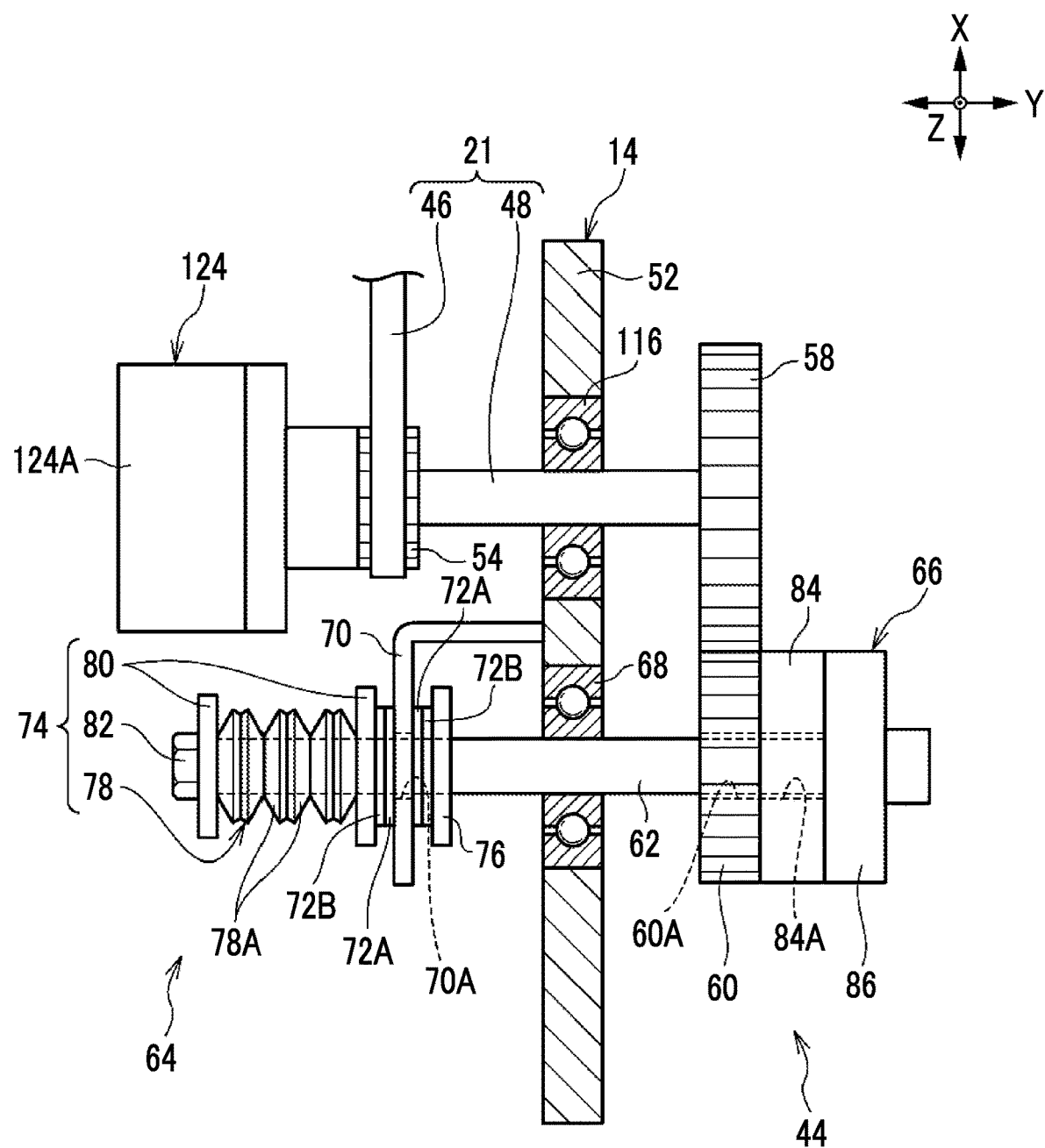
FIG. 10 is a plan view illustrating the friction mechanism and the electromagnetic brake illustrated in FIG. 9.

As illustrated in FIGS. 9 and 10, a connection portion 14 of the radiography apparatus 100 is provided with the belt 46 and the pulley shaft 48 forming the first rotation mechanism 21 and the friction mechanism 44 as in the first embodiment. The pulley 54 is fixed to the pulley shaft 48 so as to be coaxially rotatable and the belt 46 is wound around the pulley 54.

The friction mechanism 44 has the same configuration as that in the first embodiment and can be switched between a first state in which a frictional force is applied to the arm 12 and a second state in which the frictional force is not applied to the arm 12. Here, in this embodiment, in a case in which the friction mechanism 44 is in the first state, the frictional force applied to the arm 12 by the friction mechanism 44 is set to a value that is greater than at least the maximum weight of the image receiving unit 102 that can be attached to the arm 12.

Further, in this embodiment, the connection portion 14 of the radiography apparatus 100 is provided with an electromagnetic brake 124 that locks the rotation of the arm 12 by the first rotation mechanism 21 in addition to the friction mechanism 44. The electromagnetic brake 124 is connected to the pulley shaft 48 forming the first rotation mechanism 21.

The electromagnetic brake 124 is, for example, a non-excitation operation type, locks rotation in a case in which it is not energized, and unlocks rotation in a case in which it is energized. Since the electromagnetic brake 124 of the non-excitation operation type which locks rotation in a case in which it is de-energized is used, the rotation of the arm 12 is locked in a case in which the electromagnetic brake 124 is de-energized due to, for example, a power failure. Therefore, it is possible to suppress the inadvertent rotation of the arm 12.

Specifically, the electromagnetic brake 124 comprises a housing 124A in which an electromagnet (not illustrated) is provided. The pulley shaft 48 is attached to the housing 124A through a rotor (not illustrated) that is provided in the housing 124A. The housing 124A is fixed to the connection portion 14 so as not to be rotatable. The rotor and the pulley shaft 48 are rotatable with respect to the housing 124A.

The electromagnet and the rotor are disposed around the pulley shaft 48 so as to face each other in the axial direction of the pulley shaft 48, which is not illustrated. Further, in the housing 124A, a movable iron piece that is movable in the axial direction of the pulley shaft 48 is provided between the electromagnet and the rotor. The movable iron piece is disposed so as to be separated from the electromagnet and is biased toward the rotor by a biasing member (not illustrated) to press the rotor against the inner wall surface of the housing 124A.

In a case in which the electromagnetic brake 124 is not energized, the movable iron piece presses the rotor against the inner wall surface of the housing 124A so as to come into close contact therewith. Therefore, the rotation of the rotor with respect to the housing 124A is locked. In a case in which the rotation of the rotor with respect to the housing 124A is locked, the rotation of the pulley shaft 48 fixed to the rotor and the pulley 54 fixed to the pulley shaft 48 is locked and the movement of the belt 46 engaged with the pulley 54 is also locked.

As illustrated in FIG. 11, since both ends of the belt 46 are fixed to both ends of the arm 12, the orbital rotation of the arm 12 with respect to the track portion 22B is locked by the locking of the movement of the belt 46.

In contrast, in a case in which the electromagnetic brake 124 is energized, a magnetic force is generated in the electromagnet provided in the housing 124A and the movable iron piece is attracted to the electromagnet against the biasing force of the biasing member. Therefore, the pressing of the rotor against the inner wall surface of the housing 124A by the movable iron piece is released and the rotor can be rotated with respect to the housing 124A. That is, the rotation of the rotor is unlocked.

Further, in a case in which the rotation of the rotor is unlocked, the rotation of the pulley shaft 48 and the pulley 54 is also unlocked and the belt 46 engaged with the pulley 54 can be moved. Therefore, the orbital rotation of the arm 12 illustrated in FIG. 11 with respect to the track portion 22B is unlocked.

Configuration of Control Unit

As illustrated in FIG. 11, the control unit 126 of the radiography apparatus 100 controls the solenoid 116 provided at the other end of the arm 12.

In a case in which an operation of deregulating attachment and detachment is performed through the operation panel 30 (see FIG. 1) in a state in which the attachment and detachment of the image receiving unit 102 to and from the arm 12 is regulated by the solenoid 116, the control unit 126 transmits a driving signal to the solenoid 116 to energize the solenoid 116. Then, the movable iron core 116A illustrated in FIG. 8B is attracted by the solenoid 116 and the image receiving unit 102 is detachable from the arm 12.

In contrast, in a case in which a command to regulate attachment and detachment is input through the operation panel 30 (see FIG. 1), the control unit 126 de-energizes the solenoid 116. In this case, in a state in which the image receiving unit 102 is attached to the arm 12, the insertion hole 118 of the image receiving unit 102 and the through hole 114 of the base 104 communicate with each other as illustrated in FIG. 8B. Therefore, the movable iron core 116A is inserted into the insertion hole 118 of the image receiving unit 102 to regulate the attachment and detachment of the image receiving unit 102 to and from the arm 12.

In a case in which the image receiving unit 102 is not attached to the arm 12, that is, the insertion hole 118 of the image receiving unit 102 and the through hole 114 of the base 104 do not communicate with each other, it is difficult to insert the movable iron core 116A into the insertion hole 118 even though a command to regulate attachment and detachment is input. Therefore, the attachment and detachment of the image receiving unit 102 to and from the arm 12 is not regulated.

As described above, the control unit 126 controls the energization of the solenoid 116 to perform switching between a state in which the attachment and detachment of the image receiving unit 102 to and from the arm 12 is permitted and a state in which the attachment and detachment of the image receiving unit 102 to and from the arm 12 is regulated.

Further, as illustrated in FIG. 11, the control unit 126 determines whether or not the image receiving unit 102 is detached from the arm 12 on the basis of a detection signal from the photo sensor 120 provided in the arm 12.

That is, in a case in which the image receiving unit 20 is attached to the arm 12 as illustrated in FIG. 8B, the control unit 126 receives an on signal as the detection signal from the photo sensor 120. The control unit 126 determines that the image receiving unit 102 is attached to the arm 12 while receiving the on signal from the photo sensor 120.

In contrast, in a case in which the image receiving unit 102 is detached from the arm 12 as illustrated in FIG. 8A, the control unit 126 receives an off signal as the detection signal from the photo sensor 120. The control unit 126 determines that the image receiving unit 102 is detached from the arm 12 while receiving the off signal from the photo sensor 120.

Further, the control unit 126 controls the friction mechanism 44 provided in the connection portion 14 in response to an operation command from the operation panel 30. That is, in a case in which a frictional force switching command is input through the operation panel 30, the control unit 126 transmits a driving signal to the clutch 66 of the friction mechanism 44 illustrated in FIG. 9 to energize the clutch 66, thereby switching the friction mechanism 44 to the first state, as in the first embodiment. In contrast, the control unit 126 de-energizes the clutch 66 to switch the friction mechanism 44 to the second state.

Furthermore, the control unit 126 controls the electromagnetic brake 124 provided in the connection portion 14. That is, the control unit 126 de-energizes the electromagnetic brake 124 to lock the rotation of the pulley shaft 48 and the pulley 54 with respect to the housing 124A of the electromagnetic brake 124 illustrated in FIG. 9, thereby locking the orbital rotation of the arm 12 with respect to the track portion 22B.

In contrast, the control unit 126 transmits a driving signal to the electromagnetic brake 124 to energize the electromagnetic brake 124. Then, the rotation of the pulley shaft 48 with respect to the housing 124A illustrated in FIG. 9 is unlocked. Thus, the rotation of the pulley 54 is unlocked to unlock the orbital rotation of the arm 12 with respect to the track portion 22B.

Method for Controlling Radiography Apparatus

Figure 12:
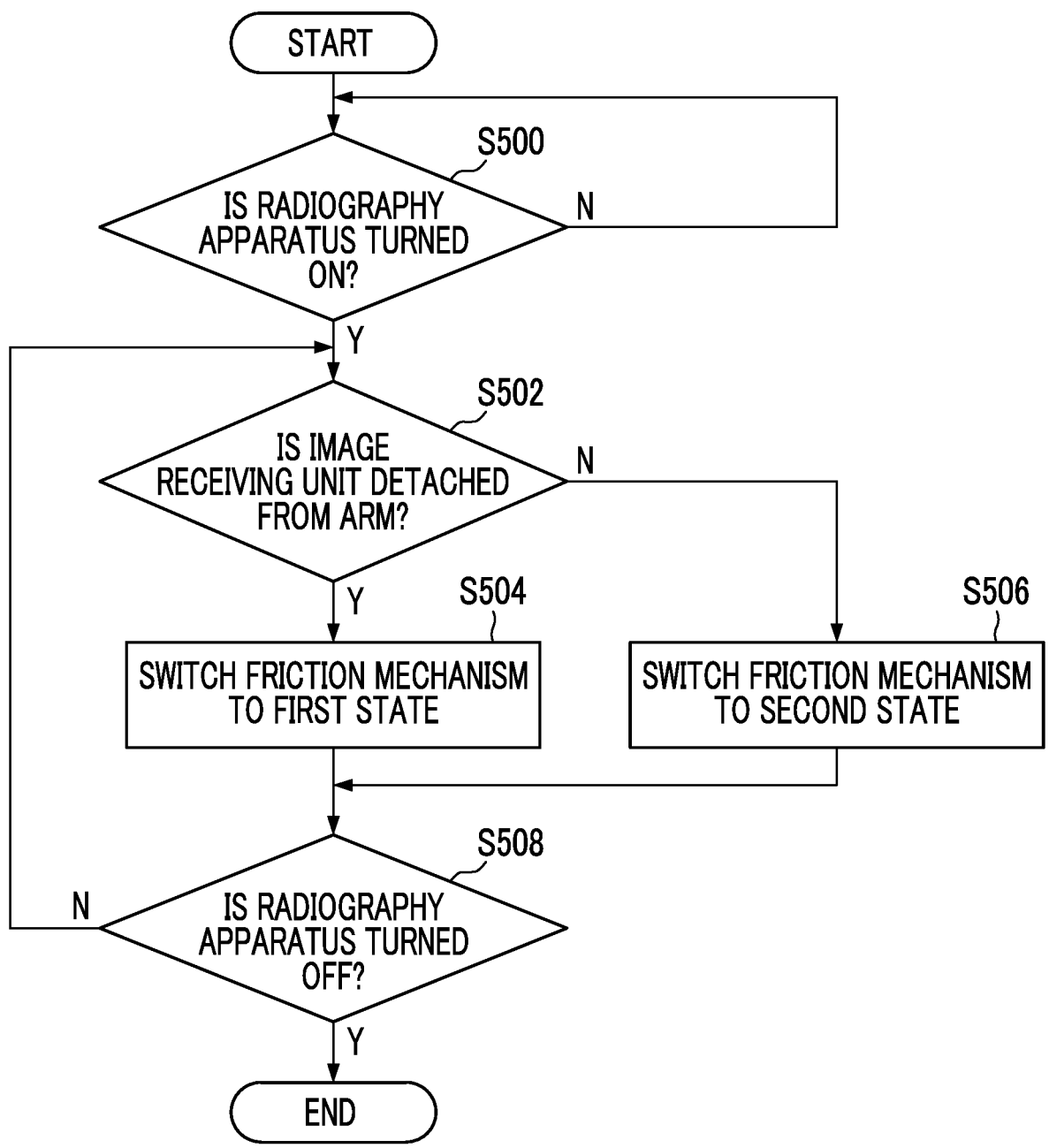
FIG. 12 is a flowchart illustrating a processing procedure of the control unit of the radiography apparatus according to the second embodiment.

Next, a method for controlling the radiography apparatus 100 according to this embodiment will be described with reference to a flowchart illustrated in FIG. 12.

First, in Step S500, in a case in which the radiography apparatus 100 is turned on by the operation of a power switch (not illustrated) (Y in Step S500), the control unit 126 starts to control the radiography apparatus 100. In a case in which the control by the control unit 126 is started, it is possible to receive the input of the imaging conditions through the operation panel 30.

In Step S502, the control unit 126 determines whether or not the image receiving unit 102 is detached from the arm 12. In a case in which it is determined that the image receiving unit 102 is detached from the arm 12 (Y in Step S502), the control unit 126 switches the friction mechanism 44 to the first state (Step S504). That is, the clutch 66 of the friction mechanism 44 illustrated in FIG. 9 is energized to connect the housing 84 and the shaft fixing portion 86.

In a case in which it is determined in Step S502 that the image receiving unit 102 is attached to the arm 12 (N in Step S502), the control unit 126 switches the friction mechanism 44 to the second state (Step S506). That is, the clutch 66 of the friction mechanism 44 illustrated in FIG. 9 is de-energized to disconnect the housing 84 from the shaft fixing portion 86.

In Step S508, the control unit 126 determines whether or not the radiography apparatus 100 has been turned off by the operation of the power switch (not illustrated) by the operator. Then, in a case in which the radiography apparatus 100 has not been turned off (N in Step S508), the process returns to Step S502. On the other hand, in a case in which the radiography apparatus 100 has been turned off (Y in Step S508), the control unit 126 ends the control of the radiography apparatus 100.

Operation and Effect

According to the radiography apparatus 100 of this embodiment, the friction mechanism 44 is connected to the first rotation mechanism 21 that rotates the arm 12 with respect to the connection portion 14, as in the radiography apparatus 10 according to the first embodiment. Therefore, the friction mechanism 44 can be switched between the first state and the second state to change a load due to the manual operation force of the arm 12.

Further, in the radiography apparatus 100 according to this embodiment, the image receiving unit 102 is attached to the arm 12 so as to be detachable. In general, in a case in which the arm 12 is rotated and the image receiving unit 102 is attachable and detachable, the arm 12 is likely to be inadvertently rotated due to a great change in weight balance during the detachment of the image receiving unit 102. Therefore, the friction mechanism 44 according to this embodiment is particularly effective for the radiography apparatus 100 in which the image receiving unit 102 is attachable to and detachable from the arm 12.

Further, the radiography apparatus 100 according to this embodiment comprises the photo sensor 120 as an example of the attachment and detachment detection unit that detects whether or not the image receiving unit 102 is detached from the arm 12. In addition, the radiography apparatus 100 comprises the control unit 126 that performs control to switch the friction mechanism 44 to the first state in a case in which the photo sensor 120 detects that the image receiving unit 102 is detached from the arm 12 and to switch the friction mechanism 44 to the second state in a case in which the photo sensor 120 detects that the image receiving unit 102 is attached to the arm 12.

As such, the friction mechanism 44 is switched to the first state, that is, the frictional force acting on the arm 12 increases in operative association with the detachment of the image receiving unit 102. Therefore, even in a case in which the image receiving unit 102 is detached, it is possible to suppress the inadvertent rotation of the arm 12.

Further, according to this embodiment, the frictional force applied to the arm 12 by the friction mechanism 44 is set to a value that is greater than at least the maximum weight of the image receiving unit 102 that can be attached to the arm 12. As such, since the frictional force in the first state of the friction mechanism 44 is greater than the weight of the image receiving unit 102, a change in the weight balance of the arm 12 in a case in which the image receiving unit 102 is detached can be absorbed by the frictional force and it is possible to further suppress the inadvertent rotation of the arm 12.

In addition, according to this embodiment, the radiography apparatus further comprises the electromagnetic brake 124 that locks the rotation of the arm 12 by the first rotation mechanism 21 and the electromagnetic brake 124 is connected to the pulley shaft 48.

As such, since the electromagnetic brake 124 is provided in addition to the friction mechanism 44, the rotation of the arm 12 is locked by the electromagnetic brake 124 to prohibit the rotation of the arm 12 as necessary. Further, since the components of the first rotation mechanism 21 are connected to the electromagnetic brake 124, the size of each mechanism can be smaller than that in a case in which the first rotation mechanism 21 and the electromagnetic brake 124 are independently configured.

Third Embodiment

Next, a radiography apparatus according to a third embodiment of the present disclosure will be described with reference to FIGS. 13 to 16. In addition, the same configurations as those in the second embodiment are denoted by the same reference numerals and the description thereof will not be repeated. The description is focused on the differences between the second and third embodiments.

Figure 13:
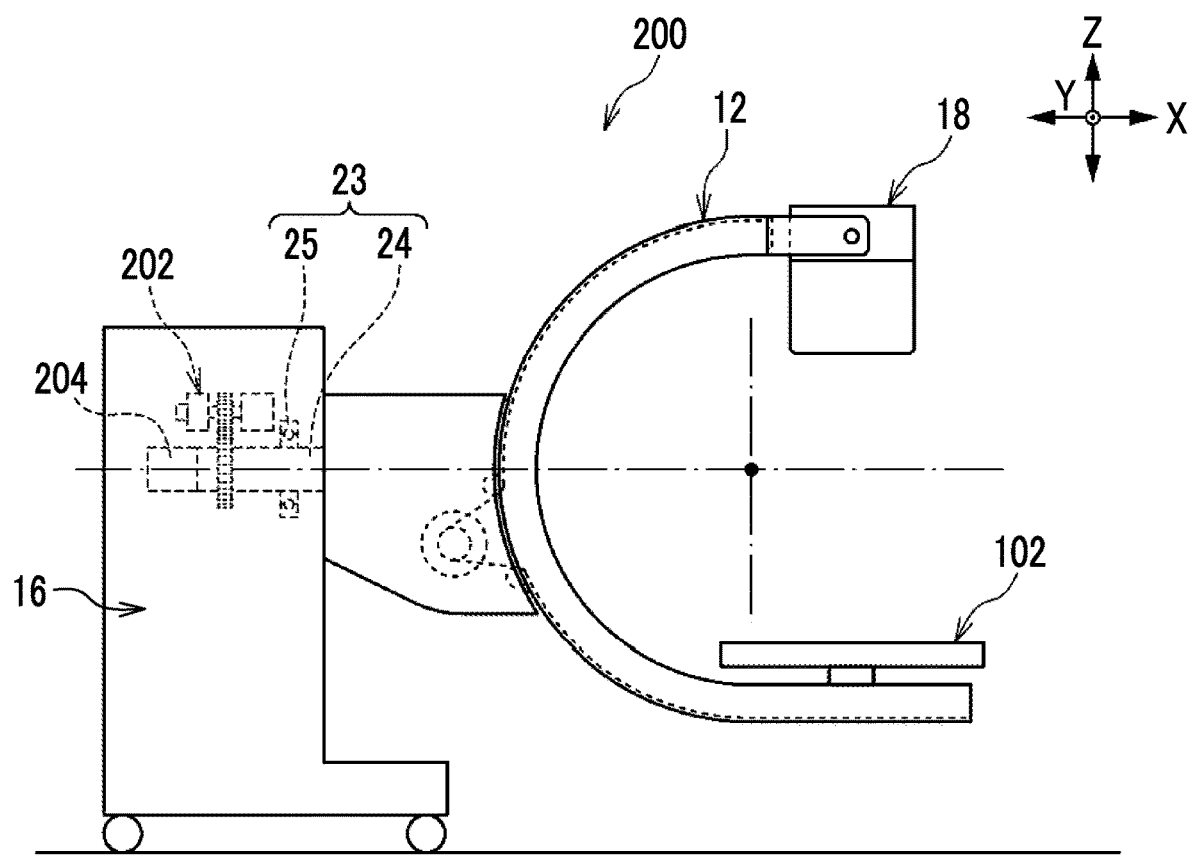
FIG. 13 is an overall side view illustrating a friction mechanism of a radiography apparatus according to a third embodiment.

In the radiography apparatus 100 according to the second embodiment, the friction mechanism 44 and the electromagnetic brake 124 are connected to the pulley shaft 48 forming the first rotation mechanism 21. In contrast, as illustrated in FIG. 13, in a radiography apparatus 200 according to this embodiment, a friction mechanism 202 and an electromagnetic brake 204 are connected to the support shaft 24 forming the second rotation mechanism 23.

Configuration of Main Body

Figure 14:
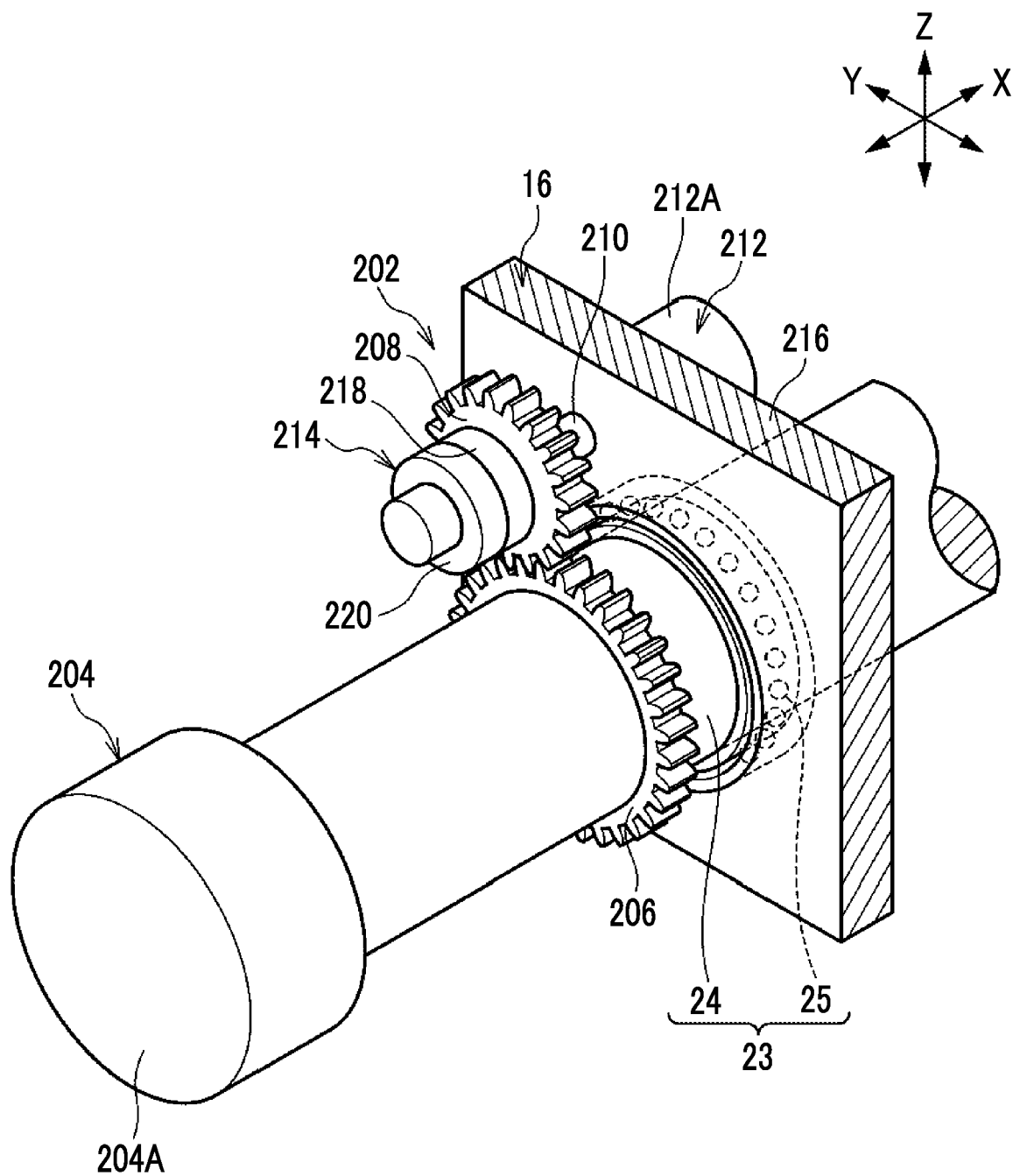
FIG. 14 is a perspective view illustrating the friction mechanism of the radiography apparatus according to the third embodiment.
Figure 15:
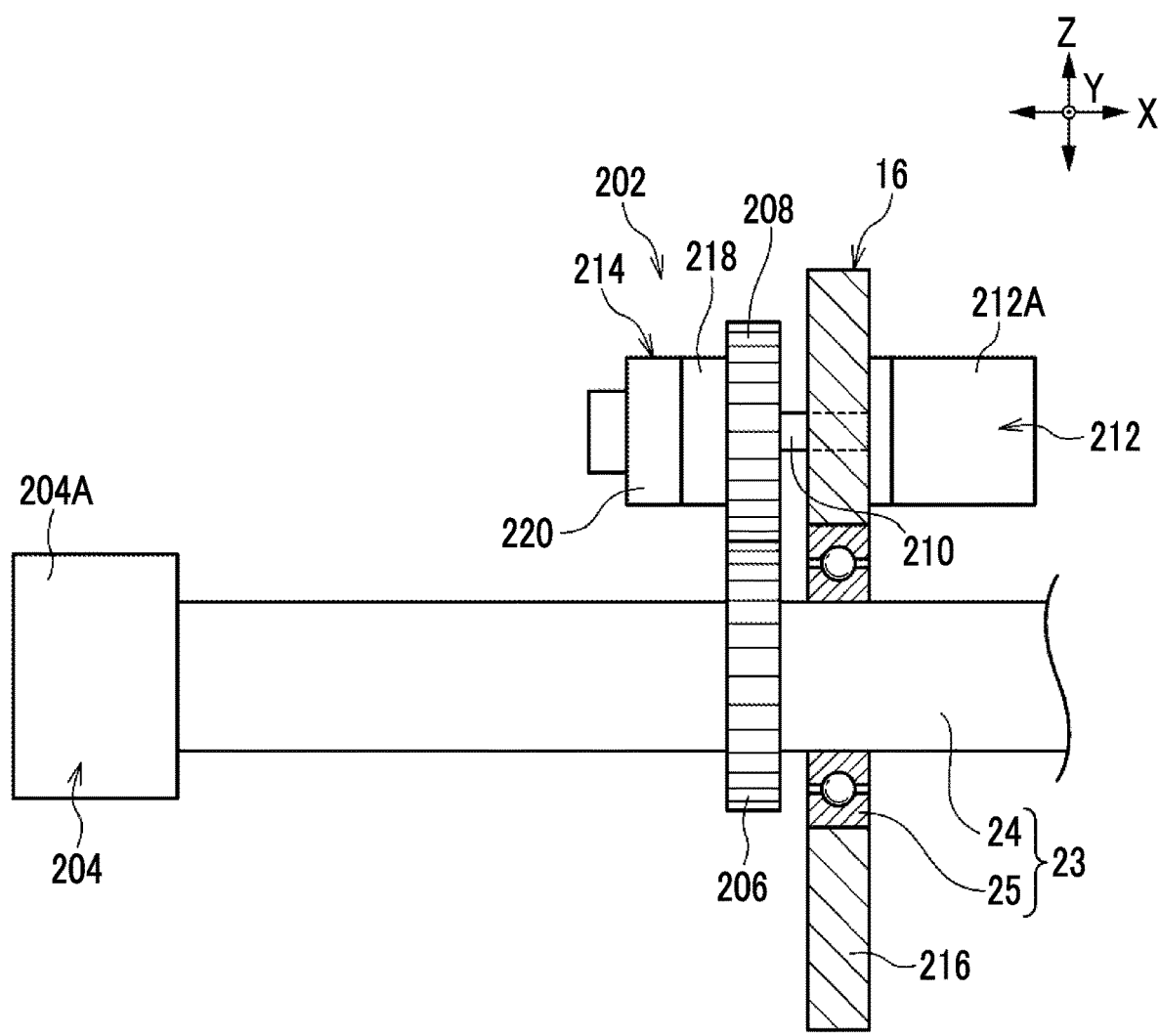
FIG. 15 is a plan view illustrating the friction mechanism illustrated in FIG. 14.

As illustrated in FIGS. 14 and 15, each of the friction mechanism 202 and the electromagnetic brake 204 is provided in the main body 16 of the radiography apparatus 200. In the main body 16, a third gear 206 is fixed to an outer peripheral surface of the support shaft 24 so as to be coaxially rotatable and a fourth gear 208 is engaged with the third gear 206.

The friction mechanism 202 includes a friction shaft 210, a frictional force generation unit 212 that is attached to the friction shaft 210 and generates a frictional force, and a clutch 214 that switches connection and disconnection between the support shaft 24 and the friction shaft 210.

The friction shaft 210 is supported by a frame 216 of the main body 16 through a bearing (not illustrated). Further, the frictional force generation unit 212 is attached to one end of the friction shaft 210 in the axial direction. In this embodiment, the frictional force generation unit 212 is, for example, a rotary damper.

Specifically, the frictional force generation unit 212 comprises a rotor (not illustrated) that is fixed to one end of the friction shaft 210 in the axial direction, a housing 212A that accommodates the rotor, and a viscous body (not illustrated) that consists of oil filled between the rotor and the housing 212A.

In a case in which the friction shaft 210 is rotated, the rotor fixed to the friction shaft 210 is rotated in the housing 212A. In this case, a frictional force acts on the outer peripheral surface of the rotor in a direction opposite to the rotation direction due to the viscous resistance of the viscous body filled in the housing 212A. That is, the frictional force acts on the friction shaft 210 in the direction opposite to the rotation direction.

The clutch 214 is attached to the other end of the friction shaft 210 in the axial direction. The clutch 214 is, for example, an electromagnetic clutch and has the same configuration as the clutch 66 according to the first and second embodiments. That is, the clutch 214 comprises a housing 218 that is fixed to the fourth gear 208 and a shaft fixing portion 220 that is fixed to the friction shaft 210.

In a case in which the clutch 214 is energized, the housing 218 and the shaft fixing portion 220 are connected to each other (corresponding to the first state). The frictional force that acts on the friction shaft 210 in a direction opposite to the rotation direction acts on the support shaft 24 through the fourth gear 208 and the third gear 206. Then, in a case in which the arm 12 illustrated in FIG. 13 is rotated about the axis, the frictional force acts on the arm 12 in a direction opposite to the rotation direction of the arm 12.

On the other hand, in a case in which the clutch 214 is de-energized, the housing 218 and the shaft fixing portion 220 are disconnected from each other (corresponding to the second state). The frictional force acting on the friction shaft 210 does not act on the support shaft 24. Therefore, the frictional force that acts on the arm 12 in a case in which the arm 12 illustrated in FIG. 13 is rotated about the axis is less than that in a case in which the clutch 214 is energized.

An electromagnetic brake 204 is attached to the other end of the support shaft 24. The electromagnetic brake 204 has the same configuration as the electromagnetic brake 124 according to the second embodiment. That is, the electromagnetic brake 204 comprises a housing 204A that is fixed to the main body 16 so as not to be rotatable. The support shaft 24 is rotatably attached to the housing 204A through a rotor that is provided in the housing 204A.

In a case in which the electromagnetic brake 204 is de-energized, a movable iron piece presses the rotor against the inner wall surface of the housing 204A so as to come into close contact therewith. Therefore, the rotation of the rotor with respect to the housing 204A is locked. Then, the rotation of the rotor with respect to the housing 204A is locked to lock the rotation of the support shaft 24 fixed to the rotor. The rotation of the support shaft 24 is locked to lock the axial rotation of the arm 12 illustrated in FIG. 13 with respect to the bearing 25.

On the other hand, in a case in which the electromagnetic brake 204 is energized, a magnetic force is generated in an electromagnet (not illustrated) that is provided in the housing 204A and the movable iron piece (not illustrated) is attracted to the electromagnet. Therefore, the pressing of the rotor against the inner wall surface of the housing 204A by the movable iron piece is released and the rotor can be rotated with respect to the housing 204A. That is, the rotation of the rotor is unlocked.

Further, in a case in which the rotation of the rotor is unlocked, the rotation of the support shaft 24 is also unlocked. Therefore, the axial rotation of the arm 12 illustrated in FIG. 13 with respect to the bearing 25 is unlocked.

Configuration of Control Unit

Figure 16:
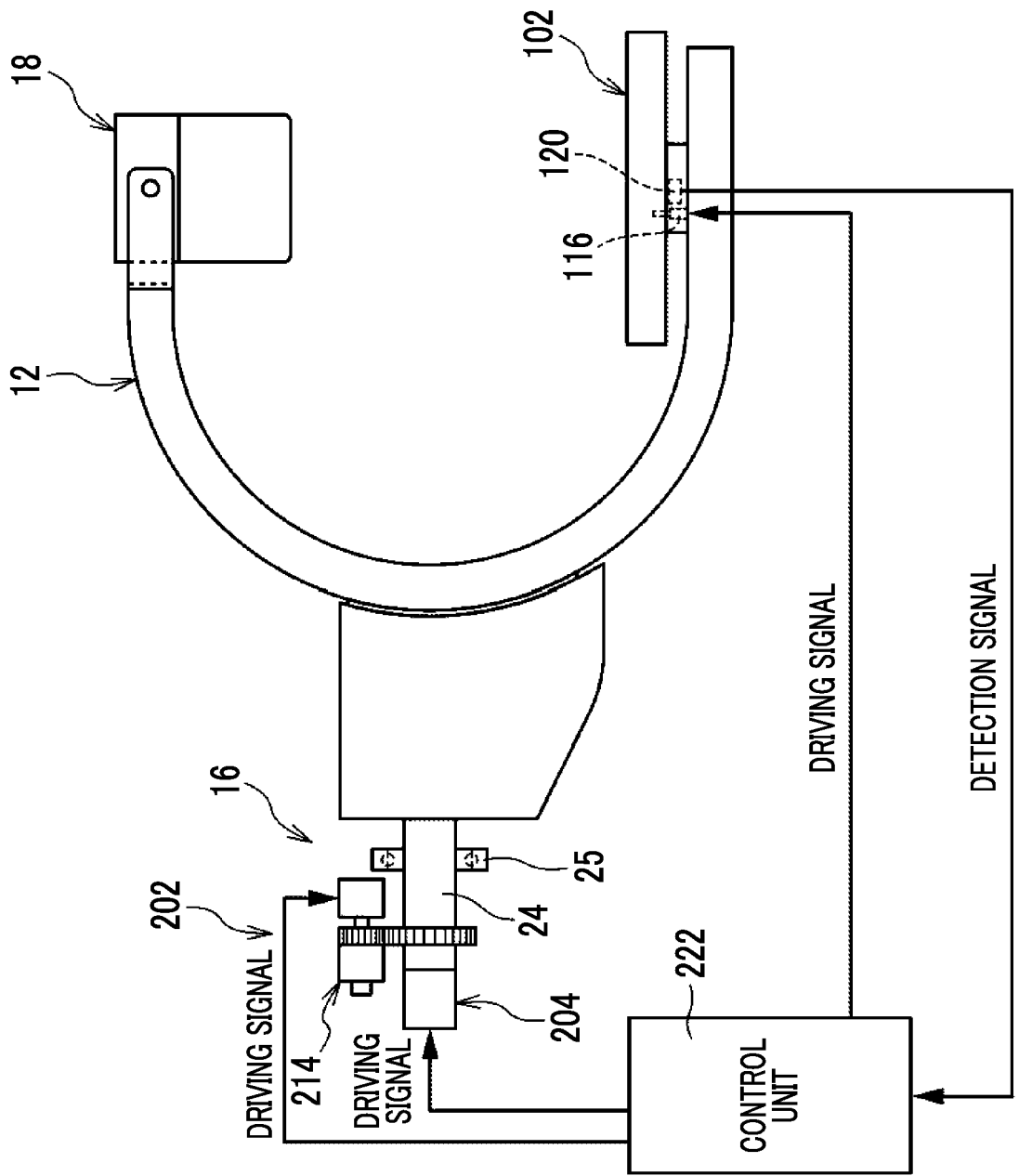
FIG. 16 is a block diagram illustrating a functional configuration of a control unit of the radiography apparatus according to the third embodiment.

As illustrated in FIG. 16, a control unit 222 controls the energization of the solenoid 116 to perform switching between a state in which the attachment and detachment of the image receiving unit 102 to and from the arm 12 is permitted and a state in which the attachment and detachment of the image receiving unit 102 to and from the arm 12 is regulated, as in the second embodiment.

Further, the control unit 222 determines whether or not the image receiving unit 102 is detached from the arm 12 on the basis of a detection signal from the photo sensor 120 provided in the image receiving unit 102, as in the second embodiment.

Further, the control unit 222 controls the friction mechanism 202 provided in the main body 16. That is, the control unit 222 transmits a driving signal to the clutch 214 of the friction mechanism 202 to energize the clutch 214, thereby switching the friction mechanism 202 to the first state. The control unit 222 de-energizes the clutch 214 to switch the friction mechanism 202 to the second state.

Further, the control unit 222 controls the electromagnetic brake 204 provided in the main body 16. That is, the control unit 222 transmits a driving signal to the electromagnetic brake 204 to energize the electromagnetic brake as in the second embodiment. Then, the rotation of the support shaft 24 with respect to the housing 204A of the electromagnetic brake 204 illustrated in FIG. 14 is locked and the rotation of the arm 12 with respect to the bearing 25 is locked.

The control unit 222 de-energizes the electromagnetic brake 204 to unlock the rotation of the support shaft 24 with respect to the housing 204A illustrated in FIG. 14. Then, the axial rotation of the arm 12 with respect to the bearing 25 is unlocked.

The control flow procedure of the control unit 222 according to this embodiment is the same as the control flow procedure of the control unit 126 according to the second embodiment. That is, as illustrated in FIG. 12, in Step S502, the control unit 222 determines whether or not the image receiving unit 102 is detached from the arm 12. In a case in which it is determined that the image receiving unit 102 is detached from the arm 12 (Y in Step S502), the control unit 222 switches the friction mechanism 202 to the first state. In a case in which it is determined in Step S502 that the image receiving unit 102 is attached to the arm 12 (N in Step S502), the control unit 222 switches the friction mechanism 202 to the second state.

Operation and Effect

The radiography apparatus 200 according to this embodiment comprises the second rotation mechanism 23 that rotates the arm 12 about the axis with respect to the main body 16 and the friction mechanism 202 that applies a frictional force to the arm 12 in a direction opposite to the direction in which the arm 12 is rotated by the second rotation mechanism 23. Therefore, similarly to the radiography apparatus 100 according to the second embodiment, the friction mechanism 202 is switched between the first state and the second state to change a load due to the manual operation force of the arm 12.

Further, according to this embodiment, the friction mechanism 202 is connected to the support shaft 24 forming the second rotation mechanism 23. As such, in the axial rotation of the arm 12, the components of the second rotation mechanism 23 and the components of the friction mechanism 202 are operatively associated with each other. Therefore, the size of each mechanism can be smaller than that in a case in which the second rotation mechanism 23 and the friction mechanism 202 are independently configured.

Further, according to this embodiment, the radiography apparatus further comprises the electromagnetic brake 204 that locks the rotation of the arm 12 by the second rotation mechanism 23. The electromagnetic brake 204 is connected to the support shaft 24.

As such, since the electromagnetic brake 204 is provided in addition to the friction mechanism 202, the rotation of the arm 12 is locked by the electromagnetic brake 204. Therefore, it is possible to prohibit the rotation of the arm 12 as necessary. Further, the components of the second rotation mechanism 23 are connected to the electromagnetic brake 204. Therefore, the size of each mechanism can be smaller than that in a case in which the second rotation mechanism 23 and the electromagnetic brake 204 are independently configured.

Other Embodiments

Examples of the embodiments of the present disclosure have been described above. However, the present disclosure is not limited to the above-described embodiments and various modifications and changes can be made without departing from the scope and spirit of the present disclosure. Further, the configurations of each of the above-described embodiments can be appropriately combined with each other.

For example, in the first embodiment, the friction mechanism 44 is connected to the first rotation mechanism 21 that orbitally rotates the arm 12. However, the friction mechanism 44 may be connected to the second rotation mechanism 23 that rotates the arm 12 about the axis. Further, the friction mechanism 44 may be connected to each of the first rotation mechanism 21 and the second rotation mechanism 23.

Further, in the first to third embodiments, the friction mechanism 44 or 202 is connected to the first rotation mechanism 21 or the second rotation mechanism 23, and the frictional force of the friction mechanism 44 or 202 is applied to the arm 12 through the first rotation mechanism 21 or the second rotation mechanism 23. However, the friction mechanism 44 or 202 may be attached to the arm 12 such that the frictional force of the friction mechanism 44 or 202 is directly applied to the arm 12.

Similarly, in the second and third embodiments, the electromagnetic brake 124 or 204 is connected to the first rotation mechanism 21 or the second rotation mechanism 23, and the first rotation mechanism 21 or the second rotation mechanism 23 is locked to lock the rotation of the arm 12. However, the electromagnetic brake 124 or 204 may be attached to the arm 12 and the rotation of the arm 12 may be directly locked by the electromagnetic brake 124 or 204.

Figure 17:
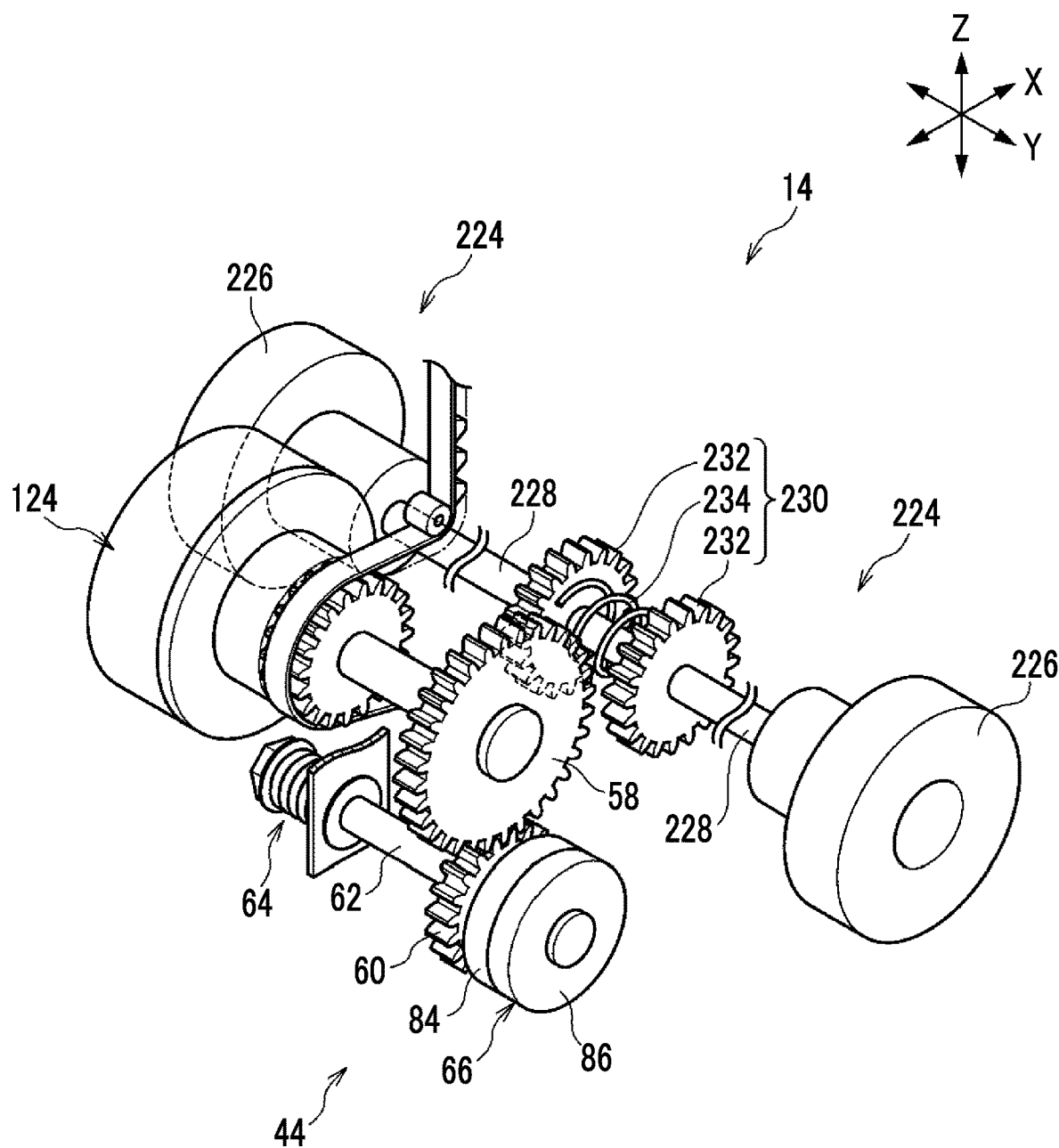
FIG. 17 is a perspective view illustrating an operation handle of a radiography apparatus according to a modification example.
Figure 18:
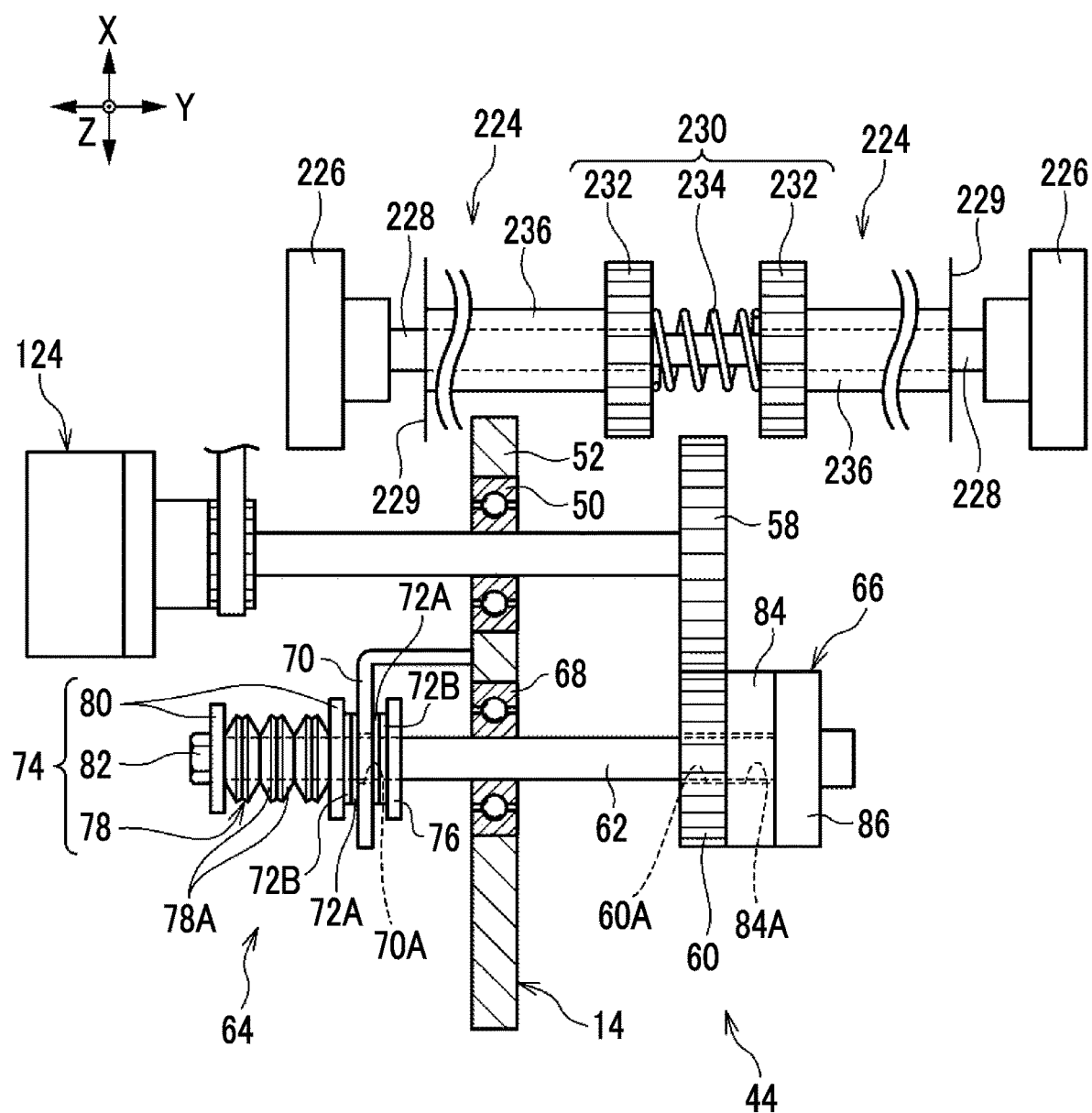
FIG. 18 is a plan view illustrating the operation handle illustrated in FIG. 17.

In addition, as illustrated in FIGS. 17 and 18 as a modification example, in addition to the friction mechanism 44 and the electromagnetic brake 124, a pair of operation handles 224 may be provided in the connection portion 14 of the radiography apparatus 100 according to the second embodiment. The pair of operation handles 224 are provided independently of the arm 12 illustrated in FIG. 11 and are manually operated to input an operation force for displacing the arm 12 to the first rotation mechanism 21.

Specifically, the pair of operation handles 224 have the same configuration and comprise a grip portion 226 and a handle shaft 228 that is fixed to the grip portion 226 so as to be coaxially rotatable. The grip portion 226 is a portion which the operator grips with hands to operate the operation handle 224. In this modification example, the grip portion 226 has a cylindrical shape that has a larger outer diameter than the handle shaft 228.

As illustrated in FIG. 18, the handle shaft 228 is disposed in parallel to the pulley shaft 48 forming the first rotation mechanism 21 and is supported by a side wall 229 of the connection portion 14 through a bearing (not illustrated) so as to be rotatable and movable in the axial direction. The handle shafts 228 of the pair of operation handles 224 are disposed on the same axis line.

Further, one end of the handle shaft 228 of the operation handle 224 is exposed from the side wall 229 of the connection portion 14 to the outside of the connection portion 14. The grip portion 226 is provided at the one end of the handle shaft 228. That is, the grip portions 226 of the pair of operation handles 224 are provided on both side surfaces of the connection portion 14 so as to protrude. Therefore, the operator can grip the grip portions 226 from both sides of the connection portion 14 and operate the operation handle 224.

A switching mechanism 230 for switching between a valid state in which the input of an operation force from the operation handle 224 to the first rotation mechanism 21 is validated and an invalid state in which the input is invalidated is provided at the other end of the handle shaft 228 located inside the connection portion 14.

The switching mechanism 230 comprises a pair of gears 232 that are fixed to the other ends of the pair of handle shafts 228 in the axial direction so as to be coaxially rotatable and a biasing member 234 that consists of, for example, a coil spring.

The pair of gears 232 face each other with a gap therebetween in the axial direction of the handle shaft 228. The first gear 58 fixed to the pulley shaft 48 is located between the pair of gears 232 in the axial direction of the handle shaft 228. In a case in which the gears 232 are moved to the other end of the handle shaft 228 in the axial direction, the first gear 58 is engaged with the gears 232.

The biasing member 234 is provided between the pair of gears 232. The gears 232 are biased by the biasing member 234 in a direction in which they become further away from each other, that is, to one end of the shaft portion in the axial direction. A spacer 236 is provided between the gear 232 and the side wall 229 of the connection portion 14. The spacer 236 is a cylindrical member into which the handle shaft 228 is inserted. The spacer 236 regulates the movement of the gear 232 to the side wall 229, that is, the movement of the gear 232 to one end of the handle shaft 228 in the axial direction.

In a case in which the operation handle 224 is operated, the operator grips one of the pair of grips 226, which are provided on both side surfaces of the connection portion 14 so as to protrude, with the hand and pushes the grip portion 226 to the inside of the connection portion 14, that is, the other end of the handle shaft 228 in the axial direction. In this case, the gear 232 of the switching mechanism 230 fixed to the other end of the handle shaft 228 in the axial direction is biased to one end of the handle shaft 228 in the axial direction by the biasing member 234. Therefore, the operator pushes the grip portion 226 against the biasing force of the biasing member 234.

In a case in which the grip portion 226 of one operation handle 224 is pushed, the handle shaft 228 is moved to the other end in the axial direction, and the gear 232 fixed to the other end of the handle shaft 228 is also moved to the other end in the axial direction. In this case, since the movement of the gear 232 of the other operation handle 224 to the one end in the axial direction is regulated by the spacer 236, the gear 232 is not moved in the axial direction and one gear 232 approaches the other gear 232 against the biasing force of the biasing member 234. Therefore, the first gear 58 disposed between the gears 232 is engaged with the one gear 232.

In a case in which the grip portion 226 is rotated with the first gear 58 engaged with the one gear 232, the handle shaft 228 and the gear 232 are rotated with the rotation of the grip portion 226 and the first gear 58 engaged with the gear 232 is rotated. Then, as the first gear 58 is rotated, the pulley shaft 48 and the pulley 54 fixed to the pulley shaft 48 are rotated. Since the belt 46 fixed to both ends of the arm 12 illustrated in FIG. 11 is wound around the pulley 54, the arm 12 is orbitally rotated as the pulley 54 is rotated. That is, the operation handle 224 can be operated to rotate the arm 12.

In the case of the other operation handle 224, similarly to the one operation handle 224, the grip portion 226 of the other operation handle 224 is pushed to engage the other gear 232 with the first gear 58. The other operation handle 224 can be operated to rotate the arm 12.

According to this modification example, the operation handle 224 makes it possible to operate the arm 12 without directly operating the arm 12. Further, since the arm 12 is displaced through the first rotation mechanism 21, the amount of displacement of the arm 12 can be adjusted more easily than that in a case in which the arm 12 is directly operated.

That is, for example, the gear ratio of the first rotation mechanism 21 can be set to adjust the relationship between the amount of rotation of the operation handle 224 and the amount of rotation of the arm 12. Therefore, the setting of reducing the amount of rotation of the arm 12 with respect to the amount of rotation of the operation handle 224 is relatively simple. The operation handle 224 makes it easy to finely adjust the amount of rotation of the arm 12.

In many cases, the arm 12 holding the irradiation unit 18 and the image receiving unit 102 is used during surgery. The operation handle 224 is provided independently of the arm 12, which makes it possible to separate an operation part operated by the operator from an operation part operated by the assistant. Therefore, the following method can also be used: the assistant rotates the arm 12 while avoiding the operation part contaminated by contact with the operator.

Figure 19:
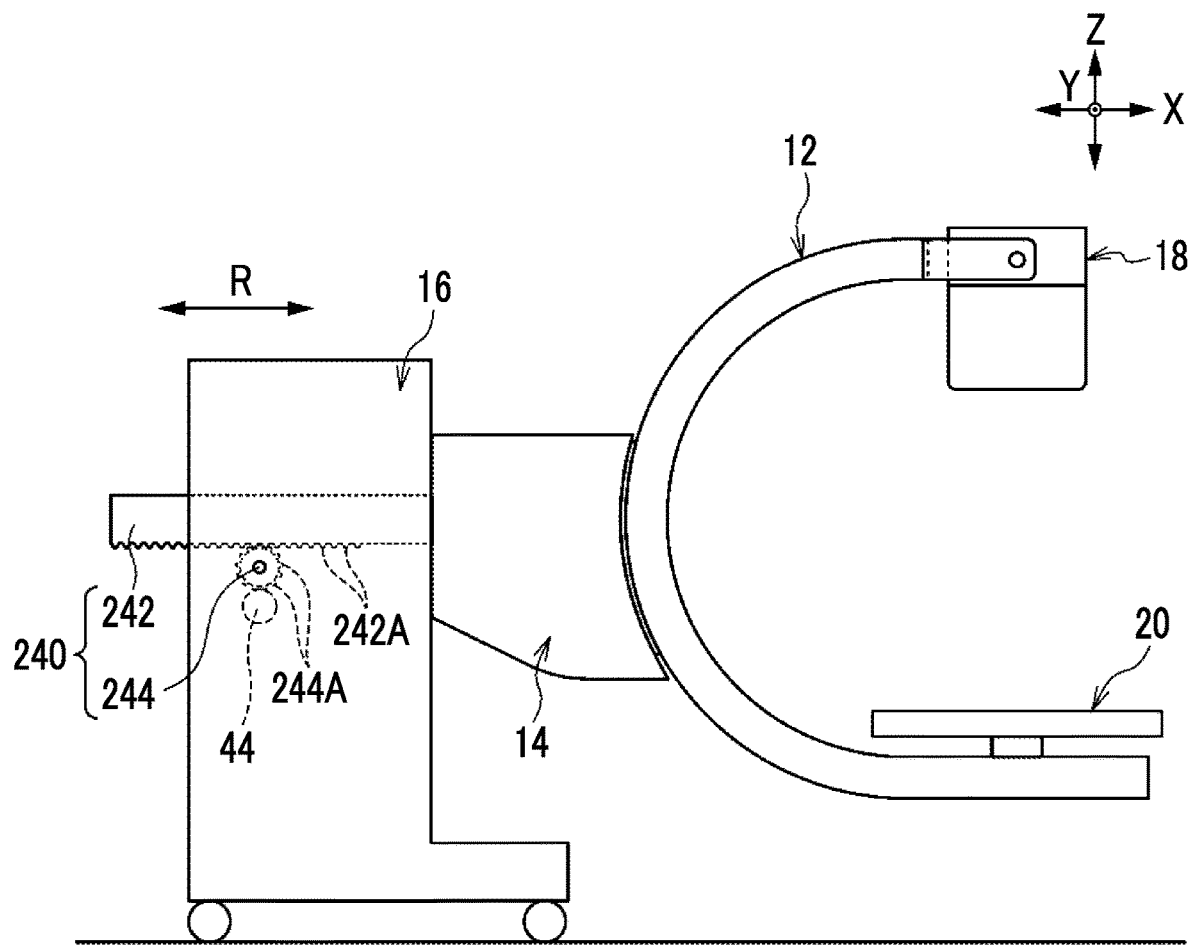
FIG. 19 is a side view illustrating a displacement mechanism of a radiography apparatus according to a modification example.

In the above-described embodiments, the displacement mechanism for displacing the arm 12 is the rotation mechanism (the first rotation mechanism 21 and the second rotation mechanism 23) that rotates the arm 12. However, the displacement mechanism for displacing the arm 12 is not limited to the rotation mechanism and may be, for example, a slide mechanism 240 that slides the arm as illustrated in FIG. 19.

Specifically, the slide mechanism 240 comprises a rack 242 that has one end fixed to the arm 12 and a pinion 244 that is provided in the main body 16. The rack 242 has a plurality of teeth 242A formed on the lower surface and is attached to the main body 16 so as to be movable in the horizontal direction (X direction). The pinion 244 is a circular gear that has a plurality of teeth 244A formed on the outer peripheral surface and is fixed to the main body 16 so as to be rotatable about the axis.

The teeth 244A of the pinion 244 are engaged with the teeth 242A of the rack 242 such that the rack 242 and the pinion 244 are operatively associated with each other. Therefore, in a case in which the arm 12 is manually slid with respect to the main body 16, the rack 242 slides in the direction of an arrow R and the pinion 244 engaged with the rack 242 is rotated.

In addition, a gear (not illustrated) is engaged with the pinion 244. The friction mechanism 44 is connected to the gear. The friction mechanism 44 has the same configuration as that in the first embodiment and can be switched between a connected state to the gear and a disconnected state from the gear by the clutch 66 (see FIG. 6).

In a case in which the clutch 66 is energized to connect the gear and the friction mechanism 44 (corresponding to the first state), the frictional force of the friction mechanism 44 acts on the pinion 244. In a case in which the rack 242 is slid to rotate the pinion 244, the frictional force acts on the rack 242 in a direction opposite to the movement direction of the rack 242. Therefore, it is possible to apply the frictional force to the arm 12.

In a case in which the clutch 66 is de-energized to disconnect the gear from the friction mechanism 44 (corresponding to the second state), the frictional force of the friction mechanism 44 does not act on the pinion 244. In this case, even in a case in which the rack 242 is slid to rotate the pinion 244, the frictional force of the friction mechanism 44 does not act on the rack 242 and the arm 12. As such, the frictional force of the friction mechanism 44 can be applied to the sliding of the arm 12.

Further, in the second embodiment, the image receiving unit 102 attached to the arm 12 so as to be detachable is a detector that is provided in the housing so as not to be detachable. However, as illustrated as a modification example in FIGS. 20A and 20B, an image receiving unit 246 that is attached to the arm 12 so as to be detachable may include a detector 248 and an accommodation portion 250.

Specifically, the detector 248 is accommodated in the accommodation portion 250 so as to be detachable and the accommodation portion 250 is attached to the arm 12 so as to be detachable. The detector 248 being attachable to and detachable from the accommodation portion 250 is synonymous with the detector 248 being attachable to and detachable from the arm 12. Therefore, this configuration makes it possible to change the size of the detector 248 attached to the arm 12.

Further, the accommodation portion 250 can also be attached to and detached from the arm 12. Therefore, in a case in which the size of the detector 248 is changed, it is easy to maintain the weight balance of the arm 12. The weights of the irradiation unit 18 (see FIG. 11) and the image receiving unit 246 held at both ends of the C-arm illustrated as an example of the arm 12 are balanced to prevent inadvertent orbital rotation and to keep the arm at any rotational position.

Specifically, the center of the orbital rotation of the arm 12 (aligned with the axis line M in FIG. 2A) is aligned with the center of gravity of the entire arm 12 including the irradiation unit 18 and the image receiving unit 246. Therefore, the arm 12 is kept at any rotational position by the effect of the weight balance of the arm 12.

In a case in which the size of the detector 248 is changed, the weight of the image receiving unit 246 is changed. Therefore, the center of gravity of the arm 12 also deviates from the center of the orbital rotation. Therefore, in addition to the detector 248, the accommodation portion 250 is attachable to and detachable from the arm 12, which makes it possible to compensate a change in the weight of the detector 248 with a change in the weight of the accommodation portion 250. As the accommodation portion 250, for example, a plurality of types of accommodation portions having different weights are prepared in which, for example, a weight adjusting ballast is changed to change the weight. The plurality of types of accommodation portions 250 are appropriately used to compensate for a weight change caused by a change in the size of the detector 248.

Therefore, even in a case in which the size of the detector 248 is changed, the accommodation portion 250 is changed according to the size change to maintain the weight balance between the irradiation unit 18 and the image receiving unit 246 and to align the center of gravity of the arm 12 with the center of the orbital rotation.

Similarly to the detectors according to the first and second embodiments, the detector 248 forming the image receiving unit 246 consists of, for example, a flat panel detector and receives the radiation which has been emitted from the irradiation unit 18 illustrated in FIG. 1 and transmitted through the subject H with an image receiving surface 248A to detect a radiographic image of the subject H. In this embodiment, the detector 248 functions as a portable electronic cassette.

The accommodation portion 250 forming the image receiving unit 246 is a box with a flat rectangular parallelepiped shape and has a fitting concave portion 252 formed in the lower surface and an accommodation concave portion 254 that accommodates the detector 248. The fitting concave portion 252 has the same configuration as the fitting concave portion 108 formed in the lower surface of the image receiving unit 102 according to the second embodiment. The fitting convex portion 106 provided at the other end of the arm 12 is fitted to the fitting concave portion 252. Therefore, the accommodation portion 250 is attached to the arm 12 so as to be detachable.

Further, similarly to the second embodiment, the arm 12 is provided with a solenoid 116 that regulates the attachment and detachment of the accommodation portion 250 to and from the arm 12 and a photo sensor 120 as an attachment and detachment detection unit. In this embodiment, the photo sensor 120 detects whether or not the accommodation portion 250 is detached from the arm 12, that is, whether or not both the accommodation portion 250 and the detector 248 forming the image receiving unit 246 are detached from the arm 12.

Figure 20A:
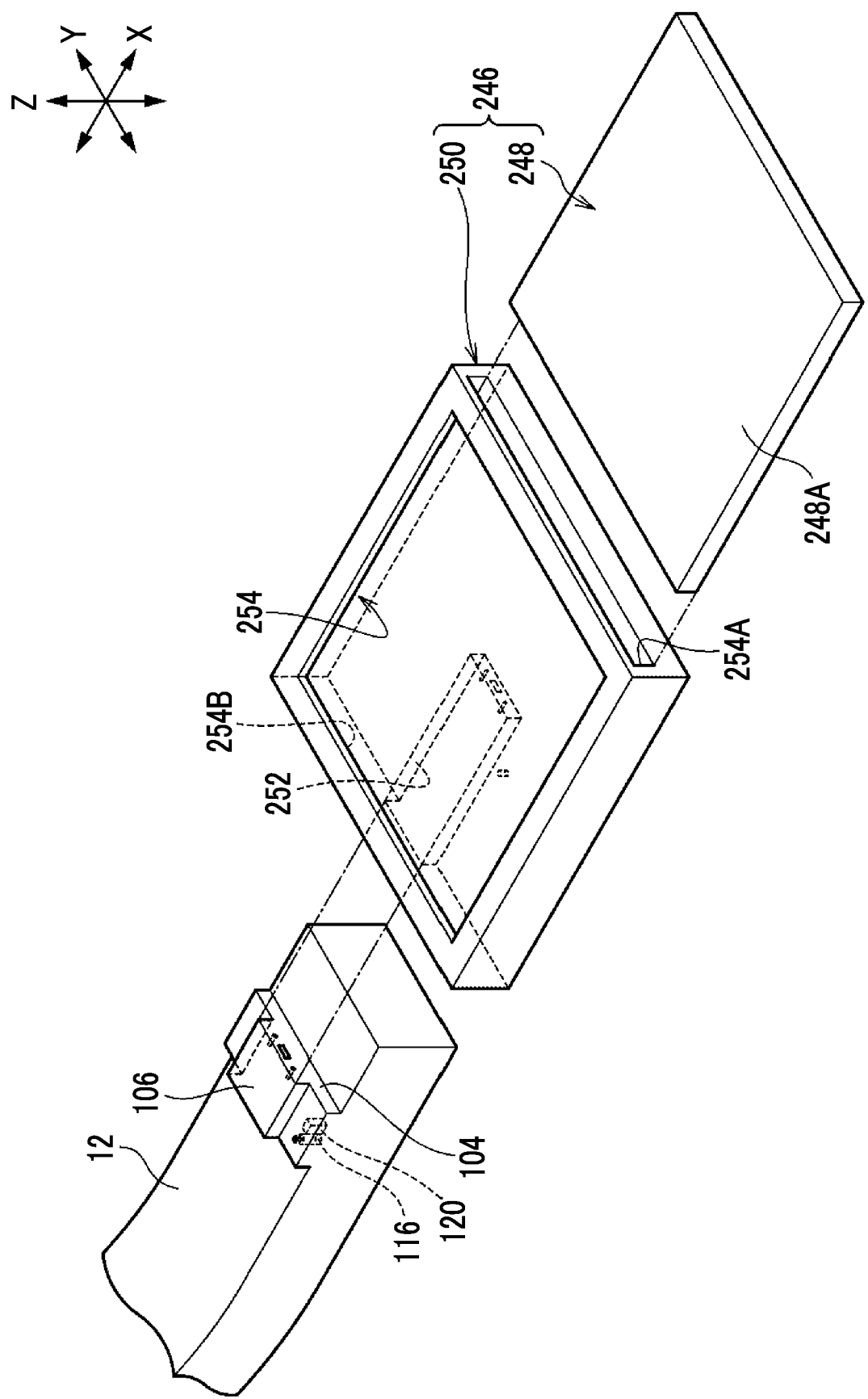
FIG. 20A is a partial perspective view illustrating an image receiving unit of a radiography apparatus according to a modification example.

As illustrated in FIG. 20A, an opening 254A for accommodating the detector 248 in the accommodation concave portion 254 is formed in one of four side surfaces of the accommodation portion 250. In addition, an opening 254B with a square shape which communicates with the accommodation concave portion 254 is formed in the upper surface of the accommodation portion 250 which faces the irradiation opening 34A (see FIG. 1) of the irradiation unit 18.

In a state in which the detector 248 is accommodated in the accommodation concave portion 254, an image receiving surface 248A of the detector 248 is exposed through an opening 254B that is formed in the upper surface of the accommodation portion 250 as illustrated in FIG. 20B. Therefore, even in a state in which the detector 248 is attached to the accommodation portion 250, that is, the arm 12, the radiation emitted from the irradiation unit 18 (see FIG. 1) can be received by the image receiving surface 248A of the detector 248.

Further, the accommodation portion 250 is provided with a photo sensor 256 that detects whether or not the detector 248 is detached from the accommodation portion 250. The photo sensor 256 is provided on a side surface of the accommodation portion 250 which is opposite to the side surface in which the opening 254A is formed in the accommodation concave portion 254.

The photo sensor 256 has the same configuration as the photo sensor 120 and detects a change in the amount of light which has been emitted from a light emitting element and then received by a light receiving element to detect whether or not the detector 248 is in the accommodation concave portion 254. The sensor that detects whether or not the detector 248 is detached from the accommodation portion 250 is not limited to the photo sensor 256 and may be, for example, a contact sensor using a piezoelectric element or a microswitch.

In addition to the photo sensor 256, an attachment and detachment regulation mechanism (not illustrated) that fixes the detector 248 in the accommodation concave portion 254 to prevent the detector 248 from falling off and releases the fixation may be provided in the accommodation concave portion 254.

In general, in a state in which the accommodation portion 250 is attached to the arm 12 and the detector 248 is detached from the accommodation portion 250, a change in the weight balance of the arm 12 is smaller than that in a state in which both the accommodation portion 250 and the detector 248 are detached from the arm 12.

Here, in this modification example, for example, the friction mechanism 44 is switched to the first state in a case in which the photo sensor 120 detects that the accommodation portion 250 is attached to the arm 12 and the photo sensor 256 detects that the detector 248 is detached from the accommodation portion 250. That is, the frictional force acting on the arm 12 is increased in operative association with the detachment of the detector 248 to suppress the inadvertent rotation of the arm 12 in a case in which the detector 248 is detached.

In addition, the frictional force of the friction mechanism 44 may be changed in three steps of a case in which the image receiving unit 246 (that is, the detector 248 and the accommodation portion 250) is attached to the arm 12, a case in which only the accommodation portion 250 is attached to the arm 12, and a case in which the image receiving unit 246 is not attached to the arm 12. In this case, it is possible to adjust the frictional force acting on the arm 12 according to the magnitude of a change in the weight balance of the arm 12.

Further, in the above-described embodiments, the arm 12 can be displaced (rotated) by only a manual operation. However, the arm 12 may be rotated by an electric operation, or the manual operation and the electric operation may be switched.

In the above-described embodiments, the first rotation mechanism 21 is configured by the track portion 22B and the pulley shaft 48 provided in the connection portion 14, the fitting portion 22A formed in the arm 12, and the belt 46 fixed to both ends of the arm 12. However, the first rotation mechanism 21 may have any configuration as long as it can orbitally rotate the arm 12 with respect to the connection portion 14 as a support portion.

For example, the first rotation mechanism may be configured by a pinion that is fixed to the rotation shaft (not illustrated) provided in the connection portion 14 so as to be coaxially rotatable and a rack (not illustrated) which is provided on the outer peripheral surface of the arm 12 and in which a plurality of teeth engaged with the pinion are formed.

In the above-described embodiments, the "second state" of the friction mechanism 44 is the state in which the frictional force of the friction shaft 62 does not act on the arm 12 (the state in which the acting frictional force is 0). However, the "second state" of the friction mechanism 44 may be a state in which at least the frictional force acting on the arm 12 is less than that in the "first state" and is not limited to the state in which the frictional force is 0. For example, the friction mechanism 44 may be switched to the "second state" by adjusting the tightening force of the nut 82 illustrated in FIG. 7 such that the frictional force acting on the friction shaft 62 is less than that in the "first state".

In the above-described embodiments, the frictional force in a case in which the friction mechanism 44 is in the "first state" is greater than the maximum weight of the image receiving unit 102 that can be attached to the arm 12. However, the frictional force in a case in which the friction mechanism 44 is in the "first state" may be less than the maximum weight of the image receiving unit 102 that can be attached to the arm 12.

In this case, the arm 12 is rotated in a case in which the image receiving unit 102 is detached from the arm 12. However, in a case in which the difference between the frictional force and the weight is small, it is possible to reduce the rotational momentum. Even in this case, the effect of reducing the rotational momentum of the arm 12 is obtained.

In the above-described embodiments, the electromagnetic clutch is used as the clutch 66 forming the friction mechanism 44. However, the clutch 66 is not limited to the electromagnetic clutch and other known clutches including a powder clutch may be used.

Further, in each of the above-described embodiments, the arm (C-arm) that can be orbitally rotated and can be rotated about the axis has been described as an example of the arm 12. However, an arm (for example, a U-arm having a U-shape in a side view) that can be only rotated about the axis may be used. Similarly to the C-arm, the U-arm can hold, for example, the irradiation unit 18 and the image receiving unit 20 or 102 in a posture in which they face each other.

In addition, X-rays have been described as an example of the radiation. However, the present disclosure is not limited to the X-rays. For example, y-rays may be used.

In each of the above-described embodiments, for example, the following various processors can be used as a hardware structure of processing units performing various processes, such as the control unit 28. The various processors include, for example, a CPU which is a general-purpose processor executing software to function as various processing units as described above, a programmable logic device (PLD), such as a field programmable gate array (FPGA), which is a processor whose circuit configuration can be changed after manufacture, and a dedicated electric circuit, such as an application-specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and/or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as the hardware structure.

Furthermore, specifically, an electric circuit (circuitry) obtained by combining circuit elements, such as semiconductor elements, can be used as the hardware structure of the various processors.

What is claimed is:

1. A radiography apparatus comprising:
an irradiation unit that emits radiation;
an arm that is capable of holding the irradiation unit and an image receiving unit that receives the radiation, which has been emitted from the irradiation unit and transmitted through a subject, in a facing posture;
a support portion that supports the arm;
a displacement mechanism, which is a rotation mechanism that rotates the arm and that displaces the arm with respect to the support portion;
a friction mechanism that is switchable between a first state in which a frictional force is applied to the arm in a direction opposite to a direction in which the arm is displaced and a second state in which the frictional force applied to the arm is less than the frictional force in the first state;
an electromagnetic brake that locks the rotation of the arm by the rotation mechanism; and
an operation panel configured to switch the friction mechanism between the first state and the second state, wherein the operation panel is a touch panel type,
wherein the rotation mechanism has a rotation shaft that is rotated with the rotation of the arm, and
the friction mechanism comprises a friction shaft, a frictional force generation unit that is attached to the friction shaft and generates the frictional force, and an electromagnetic clutch that switches connection and disconnection between the rotation shaft and the friction shaft to switch between the first state and the second state.

2. The radiography apparatus according to claim 1, wherein the arm is capable of being displaced by only a manual operation.

3. The radiography apparatus according to claim 1, wherein the image receiving unit is attachable to and detachable from the arm.

4. The radiography apparatus according to claim 1, wherein the rotation mechanism has a rotation shaft that is rotated with the rotation of the arm, and
the electromagnetic brake is connected to the rotation shaft.

5. The radiography apparatus according to claim 1,
wherein the arm has an arc shape in a side view,
the rotation mechanism includes a first rotation mechanism comprising a track portion that is provided in the support portion and supports the arm so as to be movable along the arc shape, a fitting portion that is formed in an outer peripheral portion of the arm and is fitted to the track portion, and a first rotation shaft as the rotation shaft, and
the arm is moved with respect to the track portion to be orbitally rotated about a center of the arc shape as a rotation center.

6. The radiography apparatus according to claim 1,
wherein the rotation mechanism includes a second rotation mechanism comprising a second rotation shaft as the rotation shaft that has one end fixed to the arm and a bearing that is provided in the support portion, and
the arm is rotated about the second rotation shaft with respect to the bearing to reverse positions of the irradiation unit and the image receiving unit with respect to the subject.

7. The radiography apparatus according to claim 1, further comprising:
an operation handle that is provided independently of the arm and is manually operated to input an operation force for displacing the arm to the displacement mechanism.

8. The radiography apparatus according to claim 5,
wherein the rotation mechanism further includes a belt that has one end fixed to an end of the arm at which the irradiation unit is provided and the other end fixed to an end of the arm at which the image receiving unit is provided, and
the belt is wound around the first rotation shaft.

9. A radiography apparatus comprising:
an irradiation unit that emits radiation;
an arm that is capable of holding the irradiation unit and an image receiving unit that receives the radiation, which has been emitted from the irradiation unit and transmitted through a subject, in a facing posture;
a support portion that supports the arm;
a displacement mechanism that displaces the arm with respect to the support portion;
a friction mechanism that is switchable between a first state in which a frictional force is applied to the arm in a direction opposite to a direction in which the arm is displaced and a second state in which the frictional force applied to the arm is less than the frictional force in the first state;
an attachment and detachment detection unit that detects whether or not the image receiving unit is detached from the arm; and
a control unit that performs control to switch the friction mechanism to the first state in a case in which the attachment and detachment detection unit detects that the image receiving unit is detached from the arm and to switch the friction mechanism to the second state in a case in which the attachment and detachment detection unit detects that the image receiving unit is attached to the arm,
wherein the displacement mechanism is a rotation mechanism that rotates the arm, and
wherein the image receiving unit is attachable to and detachable from the arm.

10. The radiography apparatus according to claim 9,
wherein the frictional force in the first state is greater than a maximum weight of the image receiving unit that is capable of being attached to the arm.

11. The radiography apparatus according to claim 10, further comprising:
an electromagnetic brake that locks the rotation of the arm by the rotation mechanism.

12. The radiography apparatus according to claim 10,
wherein the rotation mechanism has a rotation shaft that is rotated with the rotation of the arm, and
the friction mechanism comprises a friction shaft, a frictional force generation unit that is attached to the friction shaft and generates the frictional force, and a clutch that switches connection and disconnection between the rotation shaft and the friction shaft to switch between the first state and the second state.

13. The radiography apparatus according to claim 11,
wherein the rotation mechanism has a rotation shaft that is rotated with the rotation of the arm, and
the friction mechanism comprises a friction shaft, a frictional force generation unit that is attached to the friction shaft and generates the frictional force, and a clutch that switches connection and disconnection between the rotation shaft and the friction shaft to switch between the first state and the second state.

14. A radiography apparatus comprising:
an irradiation unit that emits radiation;
an arm that is capable of holding the irradiation unit and an image receiving unit that receives the radiation, which has been emitted from the irradiation unit and transmitted through a subject, in a facing posture;
a support portion that supports the arm;
a displacement mechanism, which is a rotation mechanism that rotates the arm and that displaces the arm with respect to the support portion;
a friction mechanism that is switchable between a first state in which a frictional force is applied to the arm in a direction opposite to a direction in which the arm is displaced and a second state in which the frictional force applied to the arm is less than the frictional force in the first state;
an electromagnetic brake that locks the rotation of the arm by the rotation mechanism; and
an operation handle that is supported by the support portion, the operation handle being provided independently of the arm and manually operated to input an operation force for displacing the arm to the displacement mechanism;
a first gear that is fixed to an end of a handle shaft of the operation handle;
a second gear configured to engage with the first gear, wherein, when the operation handle is pushed, the second gear is configured to engage with the first gear and rotate;
a pulley configured to rotate when the second gear is rotated; and
a belt would around the pulley and fixed to both ends of the arm,
wherein when the pulley is rotated, the belt is configured to orbitally rotate the arm.

15. A radiography apparatus comprising:
an irradiation unit that emits radiation;
an arm that is capable of holding the irradiation unit and an image receiving unit that receives the radiation, which has been emitted from the irradiation unit and transmitted through a subject, in a facing posture;
a support portion that supports the arm;

a displacement mechanism, which is a rotation mechanism that rotates the arm and that displaces the arm with respect to the support portion;

a friction mechanism that is switchable between a first state in which a frictional force is applied to the arm in a direction opposite to a direction in which the arm is displaced and a second state in which the frictional force applied to the arm is less than the frictional force in the first state; and an electromagnetic brake that locks the rotation of the arm by the rotation mechanism, wherein the rotation mechanism has a rotation shaft that is rotated with the rotation of the arm, and the friction mechanism comprises a friction shaft, a frictional force generation unit that is attached to the friction shaft and generates the frictional force, and an electromagnetic clutch that switches connection and disconnection between the rotation shaft and the friction shaft to switch between the first state and the second state.

* * * * *